(12) United States Patent
Cohen

(10) Patent No.: US 10,838,936 B2
(45) Date of Patent: Nov. 17, 2020

(54) COMPUTER-IMPLEMENTED METHODS, COMPUTER READABLE MEDIUM AND SYSTEMS FOR GENERATING AN ORCHARD DATA MODEL FOR A PRECISION AGRICULTURE PLATFORM

(71) Applicant: Harris Lee Cohen, Terra Bella, CA (US)

(72) Inventor: Harris Lee Cohen, Terra Bella, CA (US)

( * ) Notice: Subject to any disclaimer, the term of this patent is extended or adjusted under 35 U.S.C. 154(b) by 755 days.

(21) Appl. No.: 15/594,343

(22) Filed: May 12, 2017

(65) Prior Publication Data
US 2018/0330245 A1   Nov. 15, 2018

(51) Int. Cl.
| | |
|---|---|
| *G06N 5/04* | (2006.01) |
| *G06F 16/22* | (2019.01) |
| *G01N 33/00* | (2006.01) |
| *G06N 20/00* | (2019.01) |
| *G06N 3/04* | (2006.01) |
| *G06N 3/08* | (2006.01) |
| *G06F 30/20* | (2020.01) |
| *G06Q 50/02* | (2012.01) |

(52) U.S. Cl.
CPC ......... *G06F 16/22* (2019.01); *G01N 33/0098* (2013.01); *G06F 30/20* (2020.01); *G06N 3/0454* (2013.01); *G06N 3/08* (2013.01); *G06N 20/00* (2019.01); *G06N 5/04* (2013.01); *G06Q 50/02* (2013.01)

(58) Field of Classification Search
USPC ....................................................... 702/188
See application file for complete search history.

(56) References Cited

U.S. PATENT DOCUMENTS

| | | | |
|---|---|---|---|
| 2013/0139277 A1* | 5/2013 | Tierney | C12Q 1/02 800/275 |
| 2014/0188573 A1* | 7/2014 | Avey | G06Q 10/0639 705/7.39 |

(Continued)

OTHER PUBLICATIONS

V. Gonzalez-Dugo, D. Goldhamer, P. J. Zarco-Tejada, E. Fereres, Improving the precision of irrigation in a pistachio farm using an unmanned airborne thermal system, Irrig Sci (2015) 33: 43. doi:10.1007/s00271-014-0447-z, Springer Berlin Heidelberg.

(Continued)

*Primary Examiner* — Paul D Lee
(74) *Attorney, Agent, or Firm* — Law Office of John Stattler

(57) ABSTRACT

A computer platform implements a precision agriculture system that predicts output conditions, such as diseases, salt damage, soil problems, water leaks and generic anomalies, for orchards under analysis. The computer platform stores site and crop datasets and processed satellite image for the orchards. An orchard data learned model predicts a propensity for existence of output conditions associated with the permanent crops based on the data values for the variables of the site and crop datasets. Also, a satellite model predicts a propensity for existence of the output conditions at the orchard based on processed satellite images. A precision agriculture management model is disclosed that integrates the orchard data learned model with the satellite model to accurately predict the output conditions.

18 Claims, 41 Drawing Sheets

(56) References Cited

U.S. PATENT DOCUMENTS

| | | | | |
|---|---|---|---|---|
| 2014/0358486 A1* | 12/2014 | Osborne | ............ | G01N 33/0098 |
| | | | | 702/189 |
| 2015/0185196 A1* | 7/2015 | Coram | ................... | G01N 33/24 |
| | | | | 73/865.6 |
| 2016/0309646 A1* | 10/2016 | Starr | .................... | A01C 21/005 |
| 2017/0109395 A1* | 4/2017 | Farah | ................. | G06F 16/2358 |
| 2017/0223900 A1* | 8/2017 | Jagyasi | .................... | G06N 5/04 |
| 2017/0228743 A1* | 8/2017 | Cousins | ............ | G06Q 30/0202 |
| 2018/0075546 A1* | 3/2018 | Richt | ................. | G06Q 30/0202 |
| 2018/0146612 A1* | 5/2018 | Sauder | ................ | A01B 79/005 |

OTHER PUBLICATIONS

L. Testi, D. A. Goldhamer, F. Iniesta, M. Salinas, Crop water stress index is a sensitive water stress indicator in pistachio trees, Irrig Sci (2008) 26: 395. doi:10.1007/s00 Springer-Verlag.
Factory fresh, The Economist, Jun. 11, 2016.
Silicon Valley meets Central Valley, The Economist, Jun. 11, 2016.
Bugs in the system, The Economist, Jun. 11, 2016.
Caleb Harper, The Economist, Jun. 11, 2016.
Patrick Brown, The Application of Precision Agriculture to Tree Crops in California.
U.S. Appl. No. 15/594,306, Harris Lee Cohen.
U.S. Appl. No. 15/594,357, Harris Lee Cohen.
U.S. Appl. No. 15/594,377, Harris Lee Cohen.
U.S. Appl. No. 15/594,385, Harris Lee Cohen.
U.S. Appl. No. 15/594,414, Harris Lee Cohen.

* cited by examiner

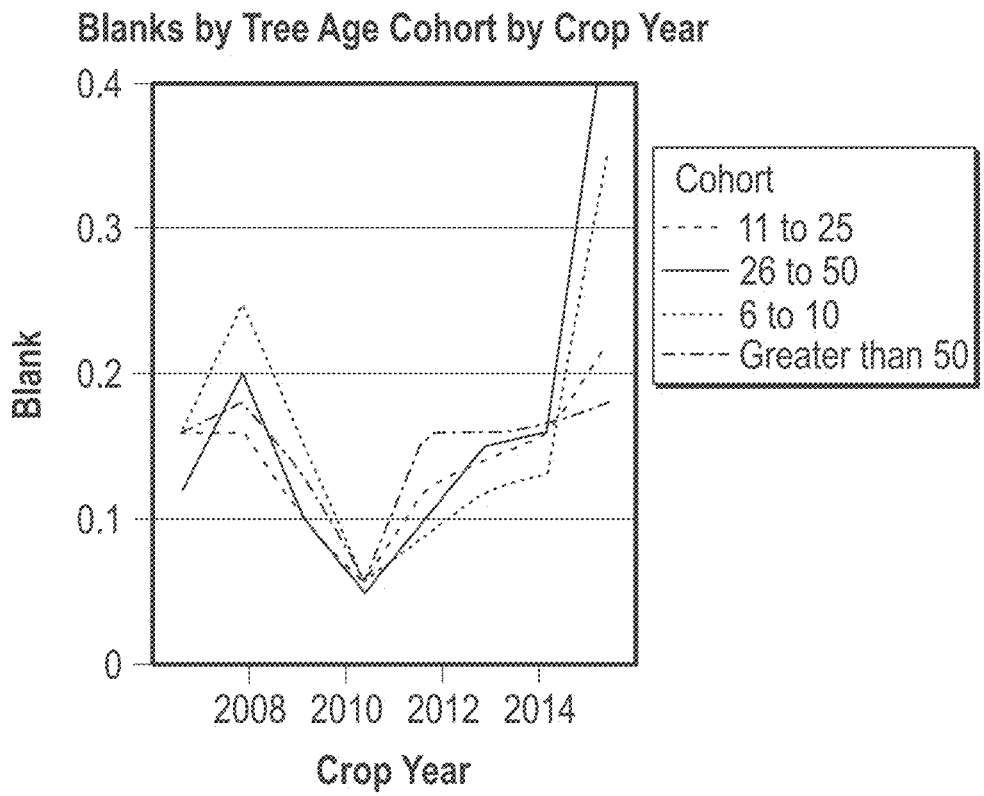
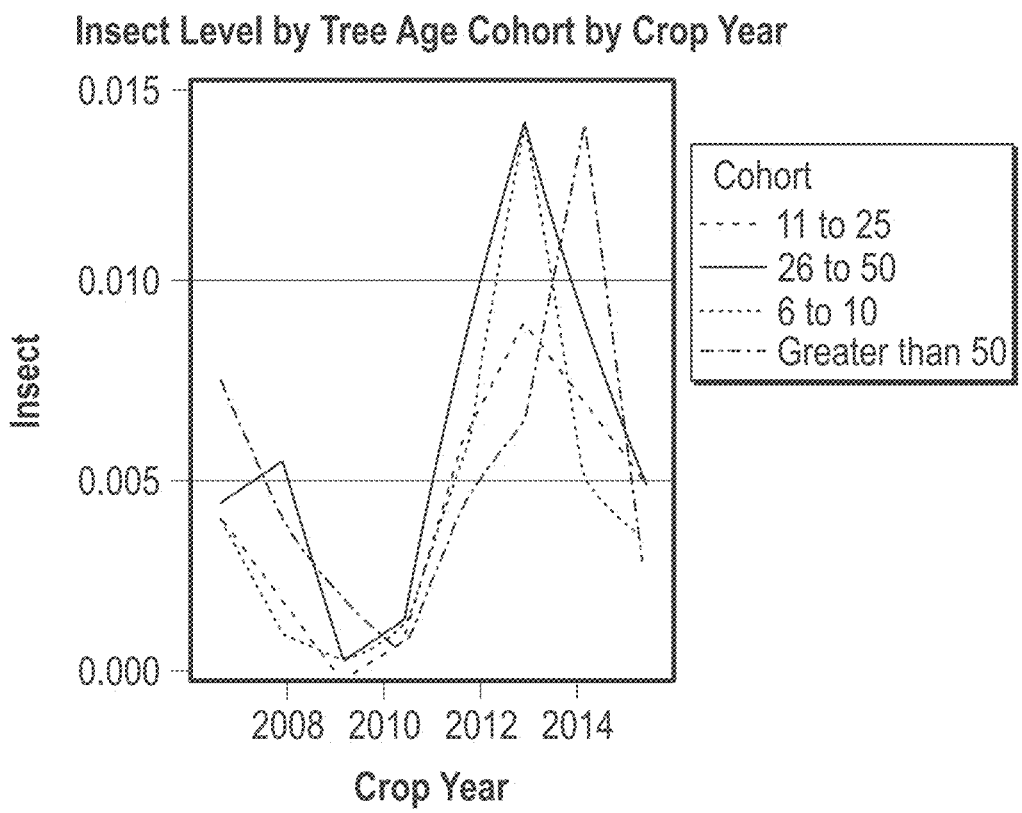
FIG. 6a

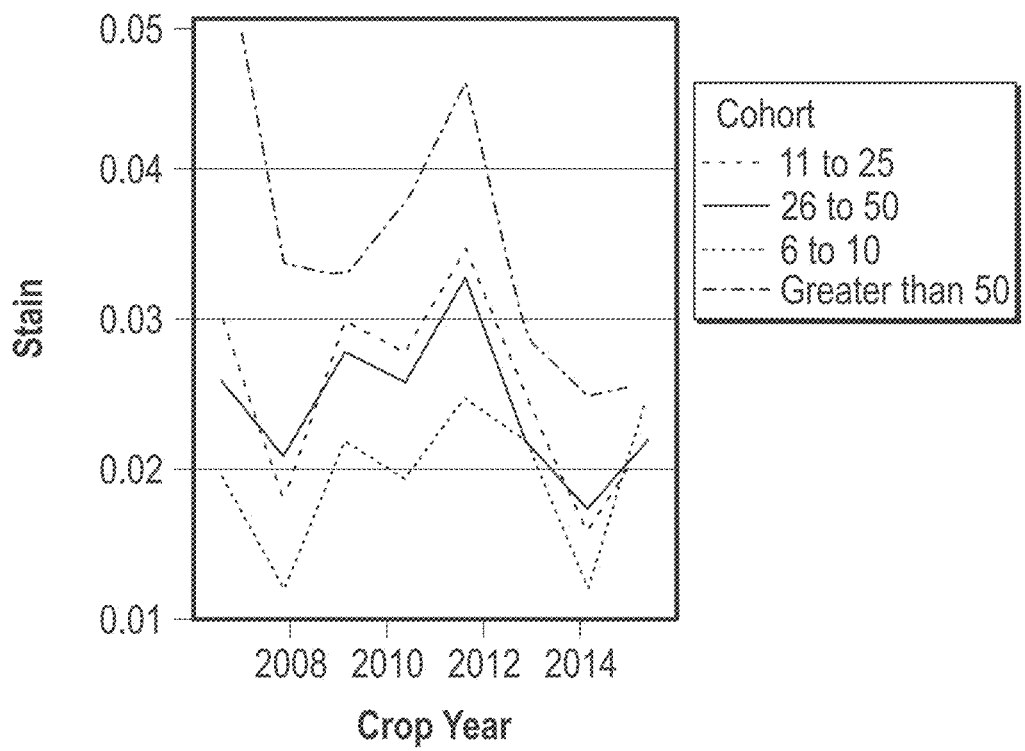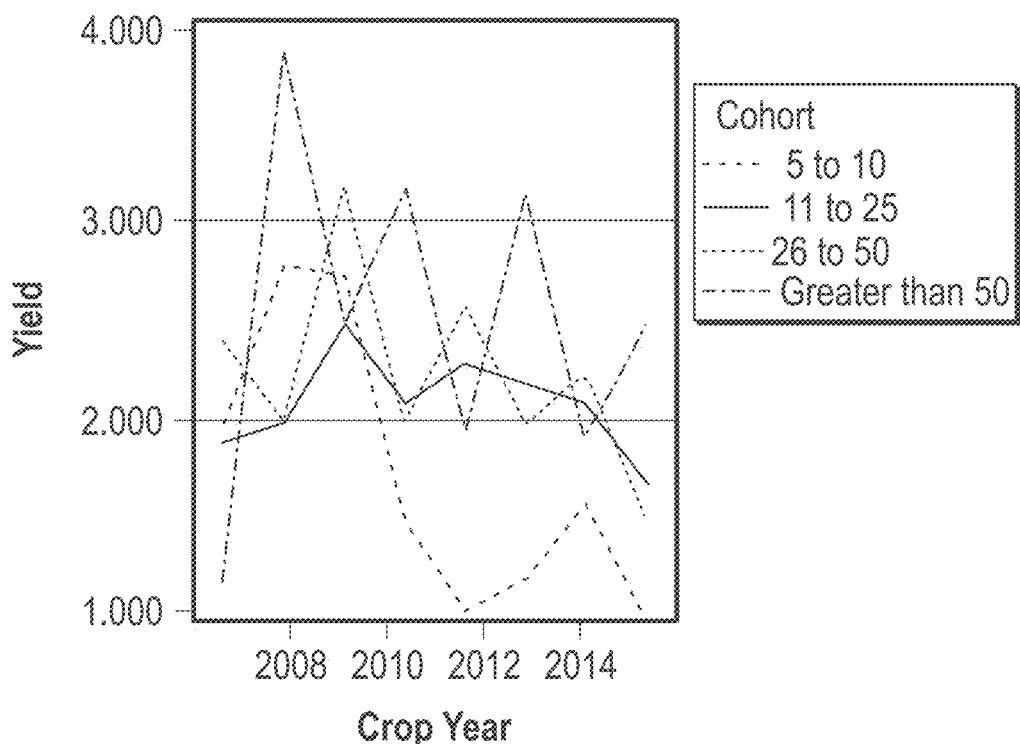
FIG. 6b

| CATEGORY NAME | DATA | DATA TYPE | DATA SOURCE | EVALUATION |
|---|---|---|---|---|
| ORCHARD DATA | TREE AGE | CATEGORICAL | PROPRIETARY | IF [0-5], [6-10], [11-25], [>25] THEN |
| | TREE DENSITY | NUMERICAL | PROPRIETARY | IF [<120], [121-145], [145-160], [>160] THEN |
| | SOIL DATA | CATEGORICAL | USGS | IF [SANDY], [LOAMY], [CLAY] THEN IF [WELL DRAINED], [AVE DRAINAGE], [POOR DRAINAGE] THEN |
| | QUALITY FACTOR (A, B, C, D, E) | NUMERICAL | PROPRIETARY | IF A/B/C/D/E [LOW], [AVG], [HIGH] THEN |
| | YIELD | NUMERICAL | PROPRIETARY | IF YIELD [LOW], [AVG], [HIGH] THEN |
| | ALTERNATE BEARING FACTOR | NUMERICAL | PROPRIETARY | IF FACTOR [LOW], [MEDIUM], [HIGH] THEN |
| | PHENOLOGY | CATEGORICAL | PROPRIETARY | IF PHENOLOGY [SPRING], [SUMMER], [FALL], [WINTER] THEN |
| SATELLITE DATA | THERMAL IMAGE | IMAGE ANALYSIS | LANDSAT8 | DETECT THERMAL ANOMALIES |
| | VEGETATION INDEX (A, B, C, D) | IMAGE ANALYSIS | VARIOUS SATELLITE | CALCULATE VEGETATIVE INDICES AND DERIVATIVES |
| WEATHER | CHILLING HOURS | NUMERICAL | NOAA | IF CHILL HOURS [<800], [801-900], [901-1000], [>1000] THEN |
| | RAINFALL | | | |

Farming Knowledge

DB

3040

Farming Knowledge Module
3010

User Interface
3020

3030

| Observed Characteristics | Output Conditions |
|---|---|
| Leaf Pigmentation (Stress) | Disease |
| Chlorophyll Ratio | |
| Leaf Senescence | |
| Soil Nitrogen | |
| Water | Water Leak |

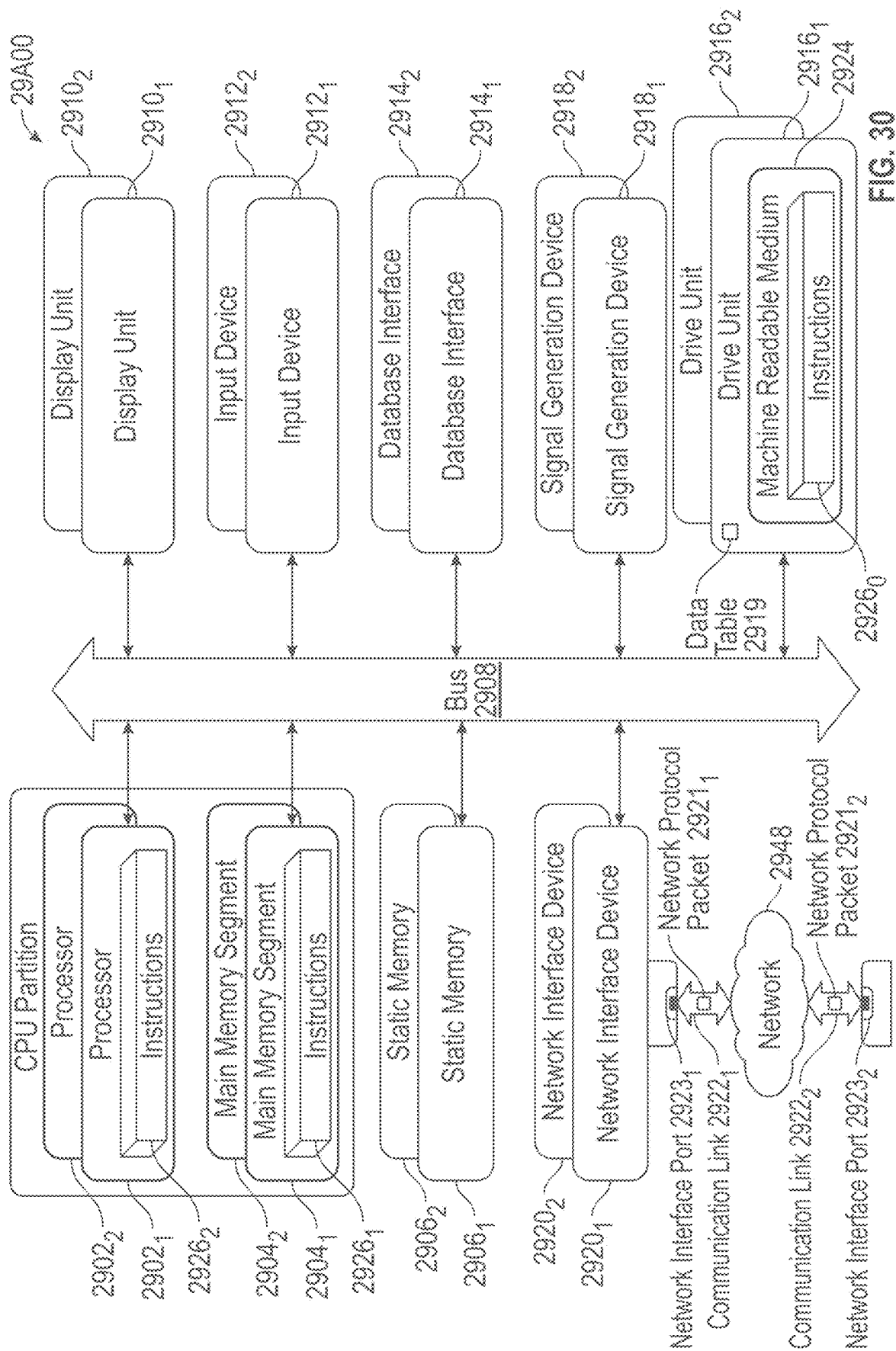

COMPUTER-IMPLEMENTED METHODS, COMPUTER READABLE MEDIUM AND SYSTEMS FOR GENERATING AN ORCHARD DATA MODEL FOR A PRECISION AGRICULTURE PLATFORM

BACKGROUND OF THE INVENTION

Field of the Invention

The present invention is related to the field of data sensing, collection and modeling, and more specifically, to computer-implemented methods, computer readable medium and systems for accumulating, managing and processing data for use in a precision agriculture system.

Art Background

The present application relates to improving outcomes in agriculture. Currently, various scientific efforts have been made to collect data and analyze various parameters related to agriculture in an attempt to improve outcomes. For example, one such parameter investigates the amount of rain water accumulated at a farm. Another such parameter may be to look at the number of chilling hours exhibited at a particular orchard. However, these scientific efforts tend to address only a single parameter at a time, and therefore analyze data in silos without the aid of data integration across multiple sources of available data. An approach, which accumulates data from multiple sources, is more robust than the silo approach, and therefore improves the ability to compute information that aids in agriculture techniques.

Information technology has taken a prominent role in many industries. For example, it's difficult to imagine conducting business in the financial world without information technology. Information technology also has applications to improve agriculture too. Although the current scientific efforts in agriculture science use analytical techniques, none take a comprehensive approach to integrate disparate datasets from diverse data sources. Therefore, what is needed is a comprehensive system that uses both state-of-the-art information technology along with all available data relevant to the cultivation of crops.

BRIEF DESCRIPTION OF THE DRAWINGS

The novel features of the invention are set forth in the appended claims. However, for purpose of explanation, several embodiments of the invention are set forth in the following figures.

FIGS. 6a-6b illustrate charts that depict quality items of pistachios tree data.

FIG. 8 illustrates one embodiment for some data structures used to define orchard data, satellite data and weather data.

FIG. 16 depicts a satellite image for an example orchard lot that highlights possible Verticillium Wilt reflectance regions.

FIG. 30 depicts a diagrammatic representation of a machine in the exemplary form of a computer system 29A00 within which a set of instructions for causing the machine to perform any one of the methodologies discussed above may be executed.

DETAILED DESCRIPTION

Although the present invention has been described in terms of specific exemplary embodiments, it will be appreciated that various modifications and alterations might be made by those skilled in the art without departing from the spirit and scope of the invention.

Precision Agriculture System

Figure 1:
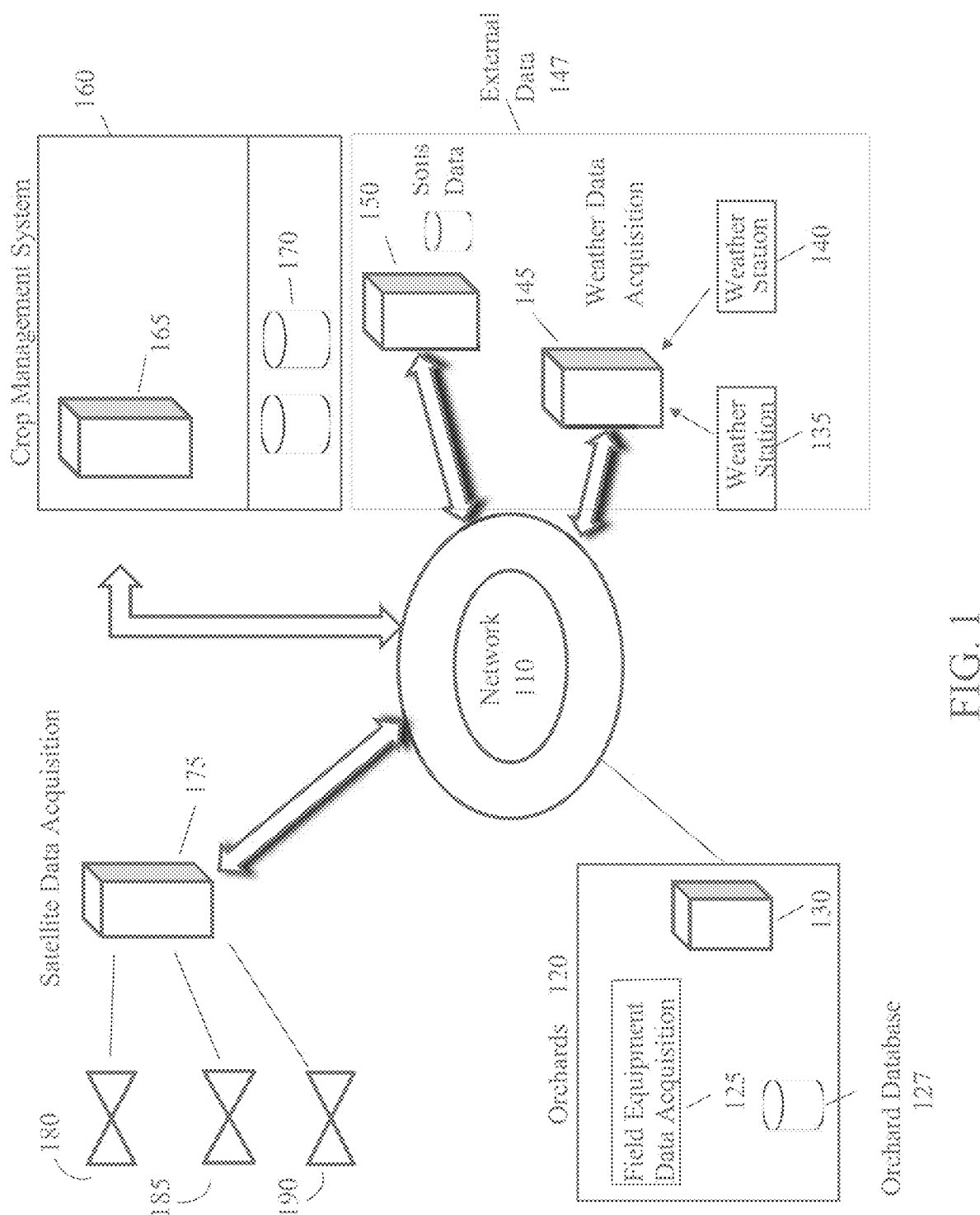
FIG. 1 is a diagram illustrating an exemplary precision agriculture remote sensing platform.

FIG. 1 is a diagram illustrating an exemplary precision agriculture remote sensing platform. In general, the platform collects data from several data sources, and aggregates the data, in crop management system 160, to aid in the precision management of permanent crops. For this exemplary embodiment, the platform acquires satellite-generated data. Various satellites acquire images of Earth's terrain, which, may be used to extract useful information regarding orchards and fields of agriculture interest. In general, the satellite images are acquired from reflections of light off the terrain as absorbed in several different spectral bands or frequencies (e.g., red, green, infrared, etc.). For example, LANDSAT8 collects images of Earth's terrain suitable for use in some aspects of the precision agriculture system. For purposes of nomenclature, the satellite image data is referred to herein as "satellite spectral data." FIG. 1 illustrates exemplary satellites (180, 185 and 190) that generate satellite spectral data for download to satellite data acquisition (175). Satellite data acquisition 175 may be a satellite service provider that acquires the satellite spectral data from one or more satellites (e.g., Digital Globe, Pleiades, RapidEye, Landsat, etc.). Regardless of the method of data acquisition, satellite data acquisition 175 transmits satellite spectral data to crop management 160 via network 110. Network 110 may comprise any type of public or private network, such as the Internet.

The precision agriculture remote sensing platform includes, for this embodiment, external data sources, such as weather data. For the exemplary embodiment illustrated in FIG. 1, weather data acquisition (145), which consists of one or more servers/computers, acquires data from one or more weather stations (135 and 140) or databases that store aggregated weather data. The weather stations (135 and 140) are located throughout the regions of agriculture interest, and collect various well-known weather metrics, including temperature, rainfall, humidity, etc. As illustrated in FIG. 1, weather data acquisition 145 collects weather data from the weather stations, and transmits the weather data to crop management system 160 via network 110.

In some embodiments, the precision agriculture remote sensing platform utilizes additional external data, such as soils data 150. In general, soils data provides information on types of soils of the fields and orchards of interest. For the exemplary embodiment of FIG. 1, soils data, stored at server/computer 150, is transmitted across network 110 to crop management system 160. The origin of soils data may come from any number of agricultural resources, including the United States Geological Survey (USGS).

In some embodiments, the precision agriculture remote sensing platform 100 utilizes data acquired directly from the farm fields and orchards. The co-location of sensing equipment in exemplary orchards 120 is illustrated in FIG. 1. For the exemplary embodiment illustrated in FIG. 1, computer/server 130 acquires data from the field through field equipment/data acquisition 125. For example, bands of frequencies, acquired from in-house radio spectrometer field studies, may be conducted as reference data. Data acquired from orchards 120 is transmitted to crop management system 160 through network 110. A further description of spectrometer field studies is described more fully below.

In some embodiments, the precision agriculture remote sensing platform further utilizes data proprietary to the orchard/farm ("orchard data") pre-stored at the crop management system. Details regarding some embodiments of orchard data are provided below.

Figure 2:
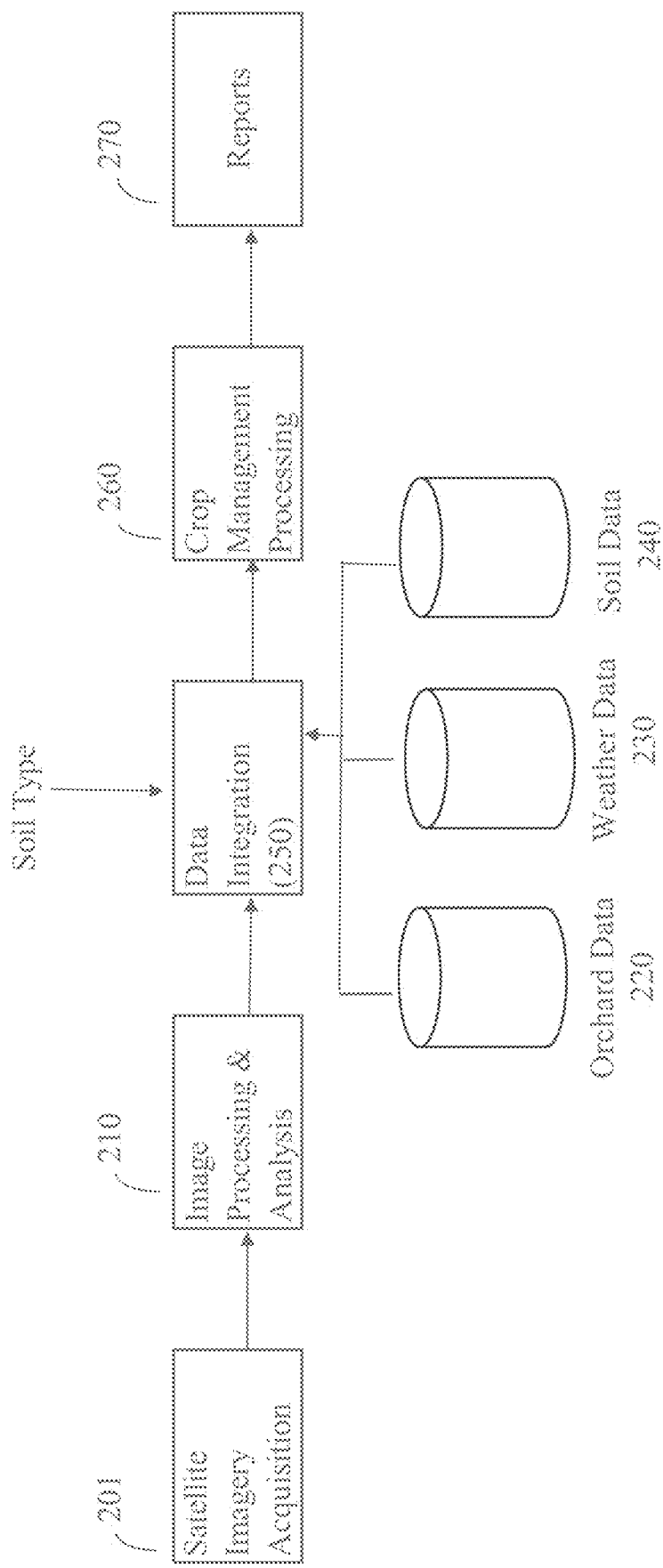
FIG. 2 is a block diagram illustrating a high-level flow of the precision agriculture remote sensing platform.

FIG. 2 is a block diagram illustrating a high-level flow of the precision agriculture remote sensing platform. Satellite spectral data is acquired in satellite imagery acquisition 201. In some embodiments, satellite imagery acquisition 201 is implemented with software routines, written in R, that process the satellite images acquired from multiple satellite sensors. The satellite imagery acquisition 201 receives, as input, GeoTiff files and processes the image to output PNGs and shapefiles.

As shown in FIG. 2, the output of satellite imagery 201 (PNGs and shapefiles) are input to image processing and analysis 210. In general, the image processing and analysis 210 implements specialized models. In some embodiments, the image processing and analysis 210 performs analysis for water leak detection, spatially correlated hotspots, plant disease, elevated soil minerals as well as crop health and severity issues. In some embodiments, the imaging processing and analysis 210 is implemented in software operating on a general purpose computer, where the custom software algorithms are written in R. The image processing and analysis comprises customized statistical algorithms using both standard vegetative indices (derive from the satellite spectral data) as well as proprietary wavelength calibrations (acquired from proprietary radio spectrometer field studies). In terms of data format, the image processing and analysis 210 receives the PNGs and shapefiles, and outputs vector data and shapefiles.

As shown in FIG. 2, the output of image processing and analysis 210 is input to data integration 250. Also input to data integration 250 are orchard data 220, weather data 230 and soil type data 240. In general, data integration 250 merges the processed satellite data with proprietary orchard data, such as yield and quality data (orchard data 220), as well as merging the data with soil types (soil type data 240) and weather conditions (weather data 230). Data integration 250 processes the data from the different data sources to generate yield, quality, and geo-coordinates for the lots. With regard to the format, data integration 250 receives, as input, shapefiles, external API data, internal database data, and generates, as outputs, vector data in shapefiles.

As shown in FIG. 2, the output of data integration 250 is input to crop management processing 260. In general, crop management processing 260 implements a model to interpret the processed data and to identify specific problems. In some embodiments, the crop management processing 260 uses twelve layers of geo-referenced data to identify problems with actionable recommendations. In some embodiments, crop management processing 260 receives, as input, vector data, shapefiles and PNGs, and outputs, vector data. In some embodiments, the crop management processing 260 produces discrete, concrete recommendations, in the form of reports 270, to resolve farming anomalies based on the assessment and conclusions of processing the algorithms. For example, the crop management processing 260 generates reports that recommend water program changes, specific soil amendment recommendations, foliar nutrient treatment options and farming practice scheduling changes.

Data & Data Sources

Figure 3A:
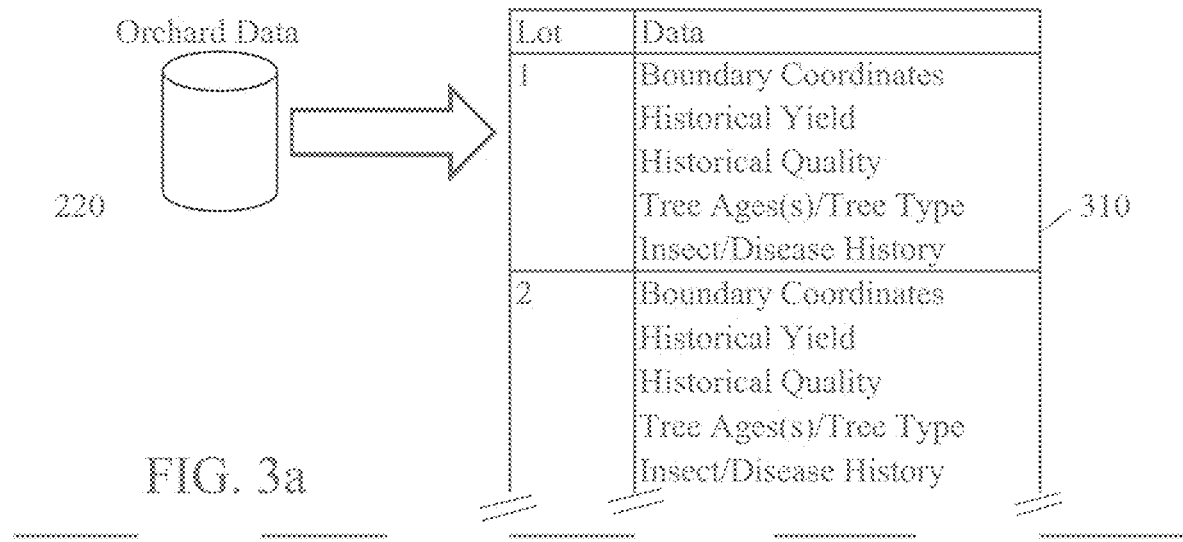
FIG. 3a illustrates the content of an example of Orchard data.

FIG. 3a illustrates the content of an example of Orchard data 220. For this example, Orchard data 220 is organized into individual lots. Although the system is described in conjunction with crop management for individual lots, any field size, such as acreage or entire farms, may be used without deviating from the spirit or scope of the invention. For the example shown in FIG. 3a, each lot (e.g., Lots 1 & 2) has corresponding data for "boundary coordinates", "historical yield", "historical quality", "tree age/tree type" and "insect/disease history." The Orchard data 220 is stored in electronic form for easy retrieval by a processing unit (processor and memory). For example, the Orchard data 220 may be stored in a relational database.

Figure 3B:
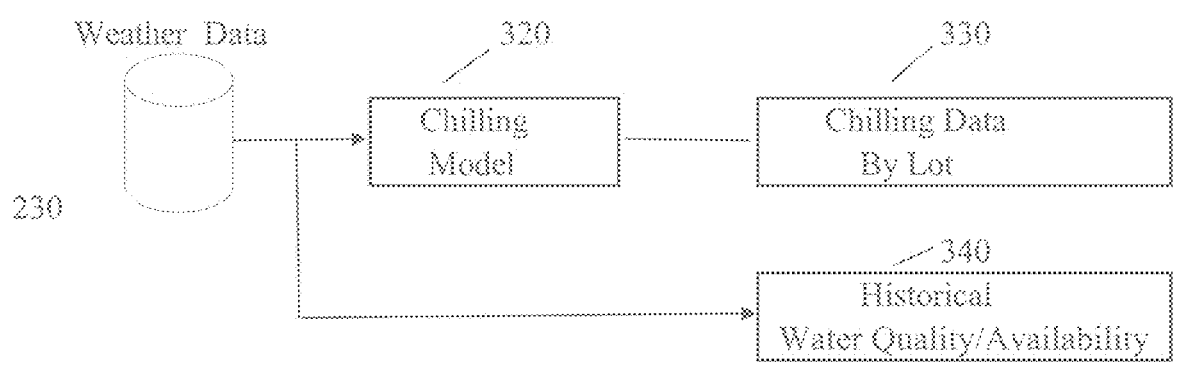
FIG. 3b illustrates a block diagram to generate historical data for weather data (330) and water availability/quality data.

FIG. 3b illustrates a block diagram to generate historical data for weather data (330) and water availability/quality data (340). As discussed above, weather data, compiled by an external source (e.g., NOAA), is retrieved from database 230. The raw weather data is used to generate one or more chilling models (block 320) described above. The chilling data may include accumulated chilling period, growing and chill portion data. The chilling data is organized by lot and stored for use in the crop management system. As shown in FIG. 3b, raw weather data is also used to generate historical water data (quality and availability), on a lot-by-lot basis, and is stored for subsequent retrieval.

Orchard Data

In some embodiments, the precision agriculture remote sensing platform analyzes orchards on a lot-by-lot basis. In other embodiments, the platform may analyze entire farms, ranches or orchards, or any segment therein, such as by acreage or by specific orchard. In order to conduct the analysis, the precision agriculture remote sensing platform acquires GID coordinates. The GID coordinates specify the boundaries of a lot. In general, the GID coordinates specify any shape of orchard or lot, such as lots defined by any polygonal shape. In some embodiments, the precision agriculture remote sensing platform provides a lot-by-lot identification (ID). For example, the platform may produce maps of orchard and farms with lines delineating the orchard or farm into lots (i.e., the lots for analysis of the system). In some embodiments, the precision agriculture remote sensing platform calculates acreages for each lot based on the known boundaries of the lot. The orchard acreage may be plotted to show acres by lot.

In some embodiments, orchard data includes a variable and data for tree age. The phenotypic expression of a tree is dependent upon the age of the tree. Because of this, orchard data incorporates tree age to interpret the physical characteristics of the tree to ascertain the output conditions. As described more fully below, tree age is broken into buckets such that a bucket is analyzed using the same criteria.

In some embodiments, orchard data further includes the variable and data for tree density. The tree density variable specifies the number of trees per area of orchard. Tree density has an effect on phenotypic expressions. As such, interpreting data of the physical characteristics of the trees is aided by knowledge of tree density. In one embodiment described more fully below, tree density is divided into four buckets for analysis.

Crop Quality Factors:

The precision agriculture remote sensing platform utilizes historical quality data that measures crop quality over some historical period. In some embodiments, the platform creates a radar chart that provides a visual pattern of historical crop quality across multiple parameters over several crop years. For example, to measure the quality of pistachios, the quality parameter measures quality of the harvested crop in terms of trash, blank shells, insects and dark stains on the crop. FIGS. 4a-4f depict six radar charts, one for each lot (lot 120 in FIG. 4a, lot 121 in FIG. 4b, lot 122 in FIG. 4c, lot 123 in FIG. 4d, lot 124 in FIG. 4e and lot 125 in FIG. 4f) that show quality data for "Insect", "Trash", "Blanks", "Adhering" and "Dark Stain", across 4 crop years (i.e., 2012-2015).

In some embodiments, the precision agriculture remote sensing platform plots, by lot, orchard quality. This is known as a choropleth map. FIGS. 5a-5f depict lot by various quality values. For this example, the quality factors of trash, insect, dark stain, blanks, closed mouth and adhering hull are shown. The percentages of the quality factor are shown for each lot.

In some embodiments, the precision agriculture remote sensing platform conducts tree age cohort analysis. For this analysis, trees are separated into individual categories or buckets based on age. For example, in some embodiments, the trees are separated into three or four cohort tree age groups. FIGS. 6a-6b illustrates charts that depict quality items of pistachios tree data, including "blanks", "insect", "stain", and "yield" in the vertical portion of the graph, plotted against crop year in the horizontal axis. As shown in FIGS. 6a-6b, each plot corresponds to a cohort group classified by tree age (i.e., 11 to 25, 26 to 50, 6 to 10, and greater than 50).

Figure 7:
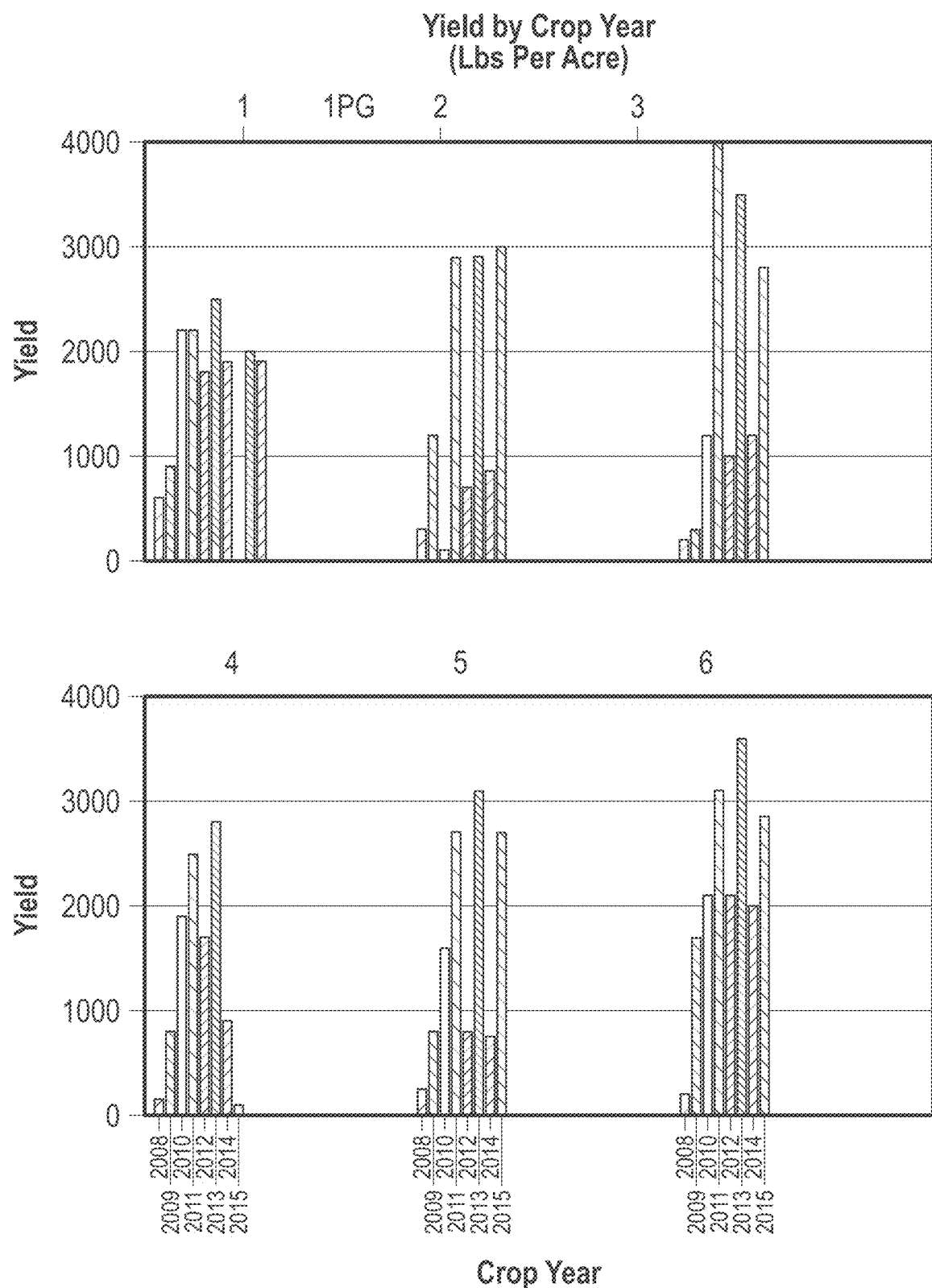
FIG. 7 shows a graph that depicts yield by lot for several example years

Yield by Lot:

In some embodiments, the precision agriculture remote sensing platform determines yield of the crop. Some permanent crops, such as pistachios, are alternate bearing crops with yields that vary from year to year (i.e., one high yield year followed by a low yield year). As such, historical crop yield is an important input to interpret sensed data. FIG. 7 shows a graph that depicts yield by lot for several example years.

FIG. 7 depicts, for an example orchard plot, soil type relative to the percent of closed mouth vegetation. This example shows, for loamy and mixed soil types, various percentages of trees with closed mouth vegetation.

In some embodiments, the orchard data includes data for phenology. The phonology variable identifies the phase of the tree as signified by the season (e.g., spring, summer, fall and winter). Of course, the phenotypic expressions of the tree will very throughout the seasons. As such, the phonology variable provides context when interpreting the data on the physical characteristics of the trees.

The orchard data further includes, as a variable, alternate—bearing factor. Certain trees, including pistachio trees, alter their production and yield of fruit from year to year. A tree that produces lots of fruit one year is expected to produce much less fruit the following year. The alternate—bearing factor is an important variable to interpret characteristics of permanent crops, such as trees, when assessing potential problems with the tree.

External Data

In some embodiments, external data (i.e., not proprietary to the orchard) is used to identify output conditions. One type of external data is weather data. In some embodiments, the precision agriculture remote sensing platform uses the weather data as an important input to interpret the conditions of an orchard. Weather data may include both the variables "chilling hours" and "rainfall." The rainfall variable indicates the amount of annual rainfall received in an orchard. Temperatures, used to create chilling data, may be collected from weather stations. This temperature data is used to create chilling models that depict a wide range of temperatures a tree has been exposed to during the growing season. Various models may be used to create chilling data, such as "Growing Degree Hours", "Utah Model", "Dynamic Model" and "Crossa-Raynaud model." The historical chilling data provide data for both chill portions and chill hours. As described more fully below, in some embodiments, the chilling hours is broken into four buckets for analysis.

In some embodiments, the precision agriculture management system uses, as a type of external data, soil data. Soil data may include both soil type as well as a characterization of soil drainage. For example, in one embodiment, soil data includes the soil types of "Sandy", "Loamy", and "Clay." Soil drainage may be characterized as "well drained."

Satellite Data

Figure 3C:
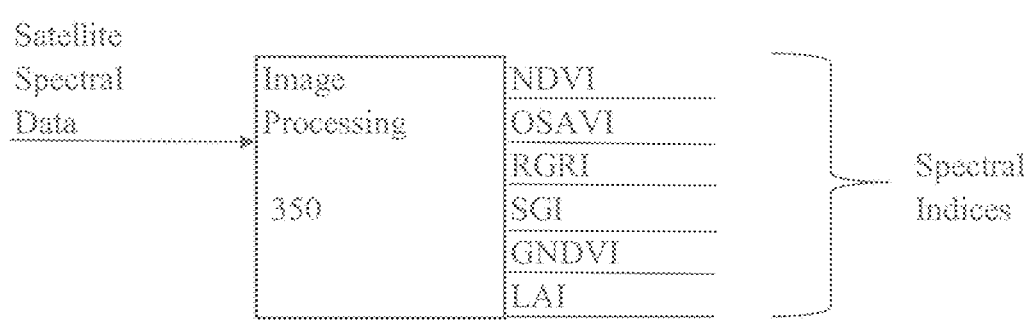
FIG. 3c, shows a block diagram illustrating one embodiment for satellite image processing.
Figure 4A:
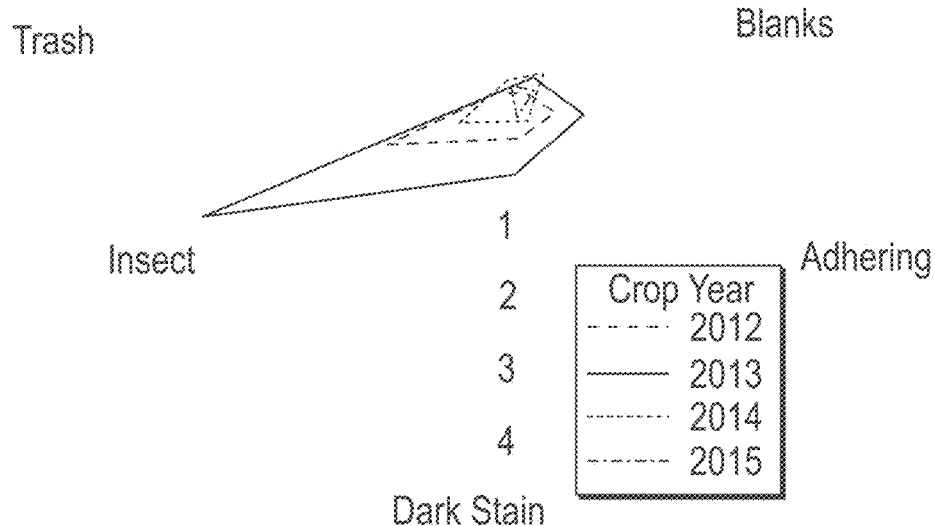
FIGS. 4a-4f depict six radar charts, one for each lot, across 4 crop years.
Figure 4B:
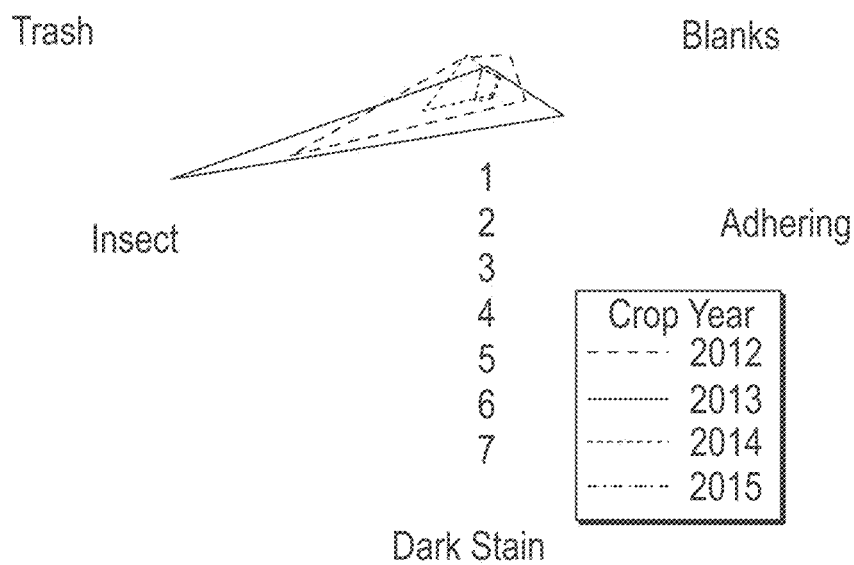
Figure 4C:
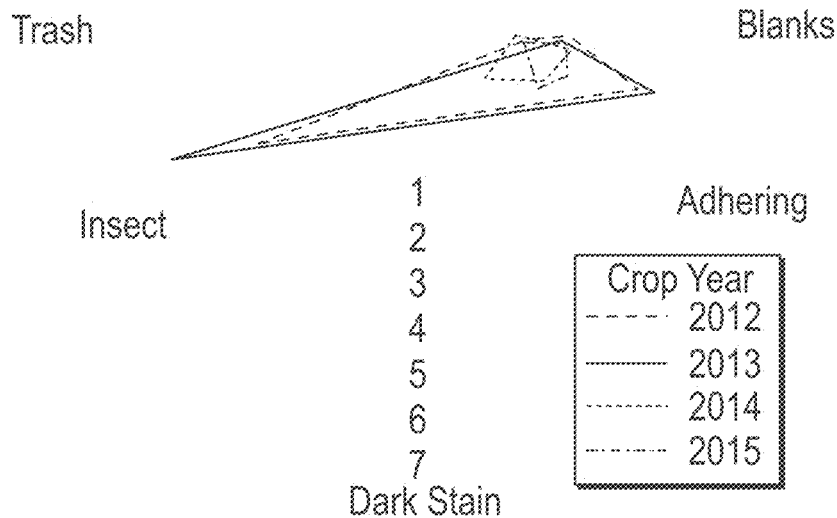
Figure 4D:
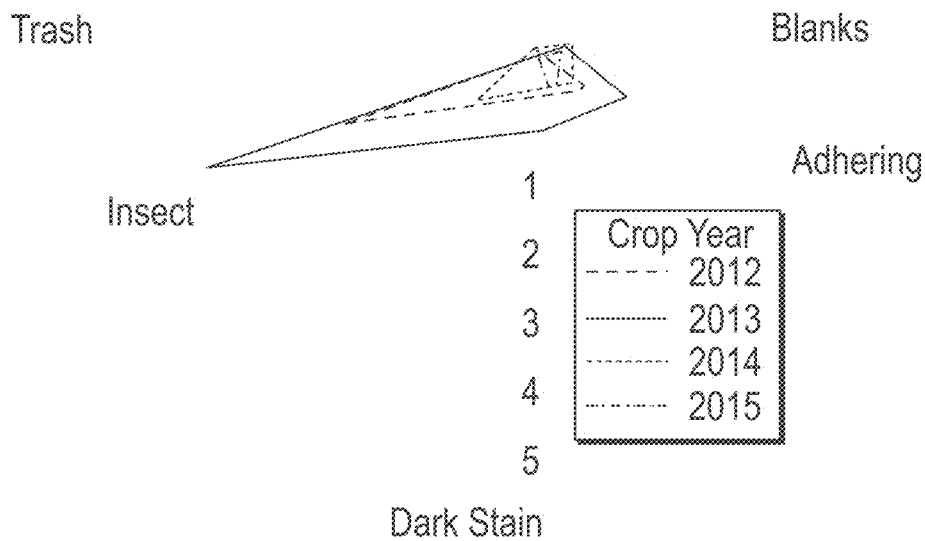
Figure 4E:
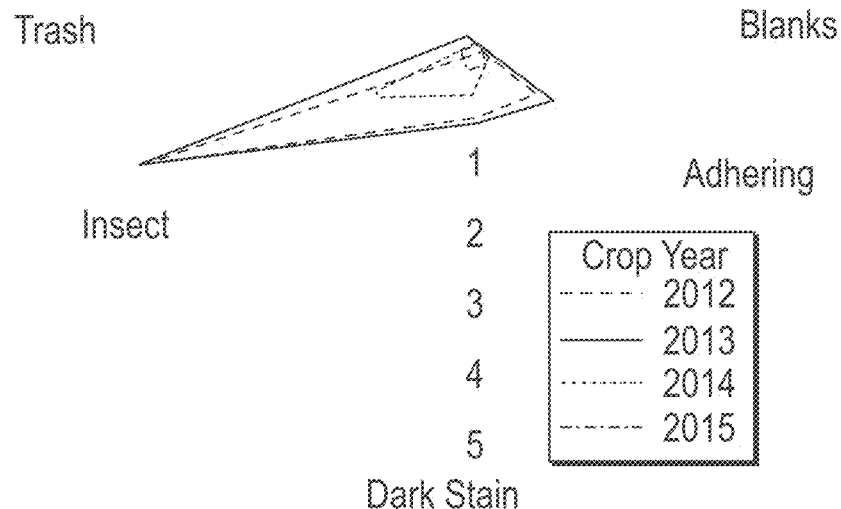
Figure 4F:
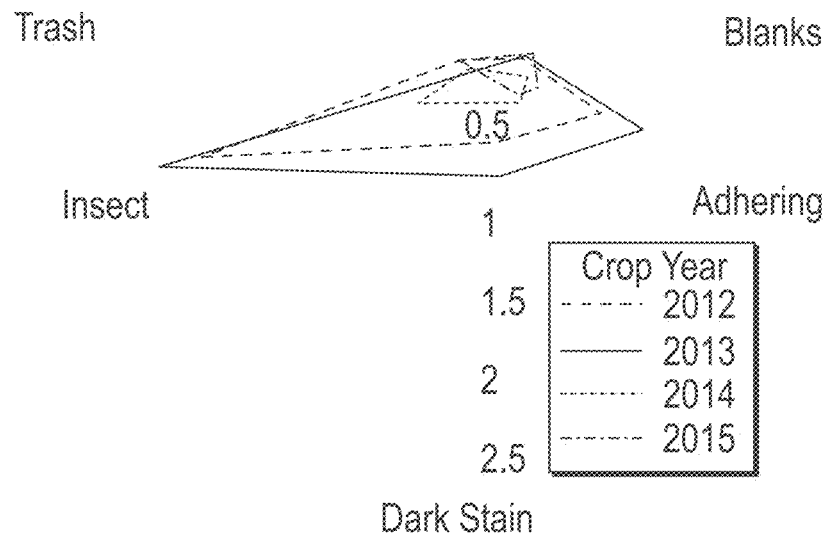
Figure 5A:
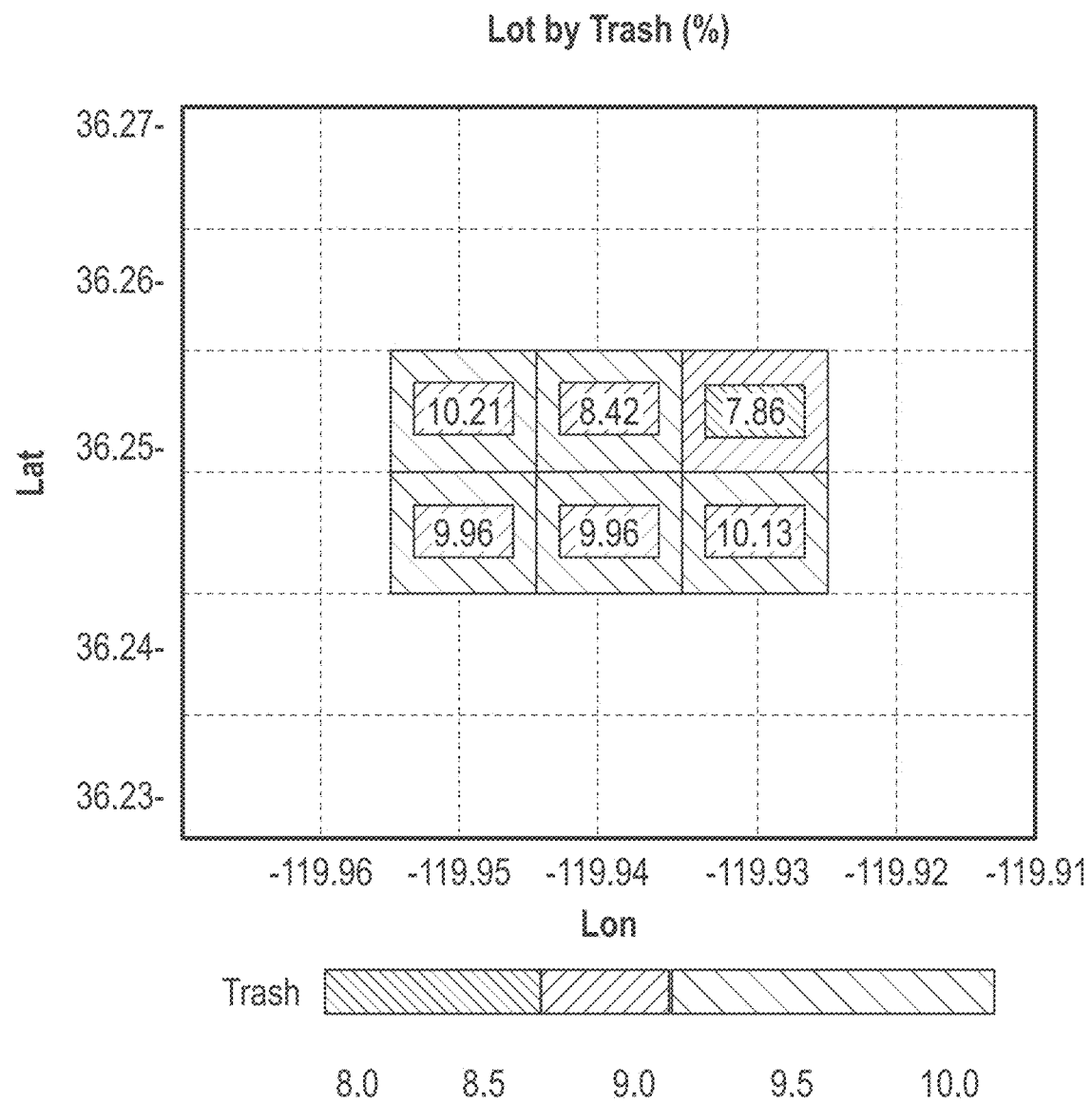
FIGS. 5a-5f depict lot by various quality values.
Figure 5B:
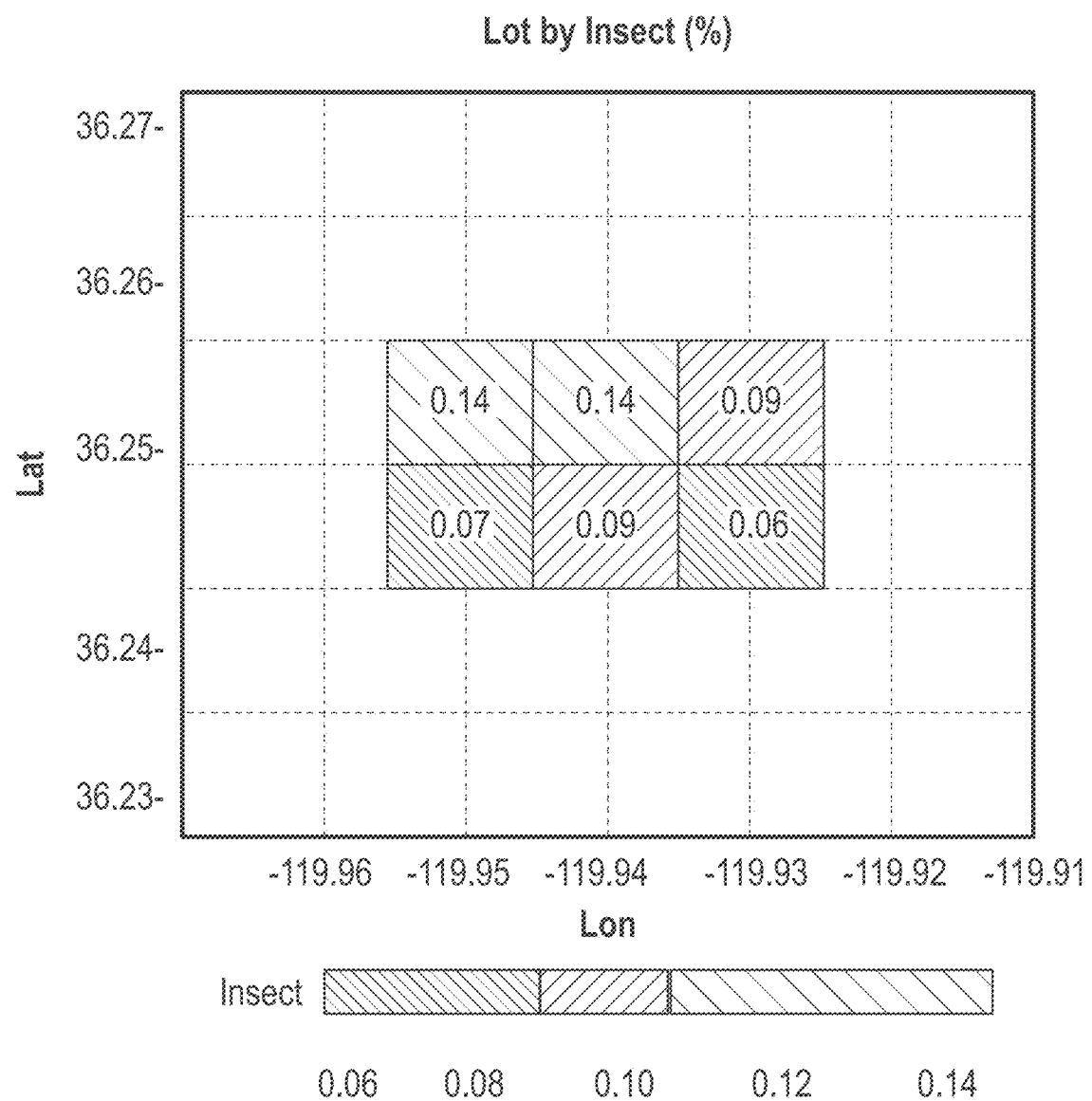
Figure 5C:
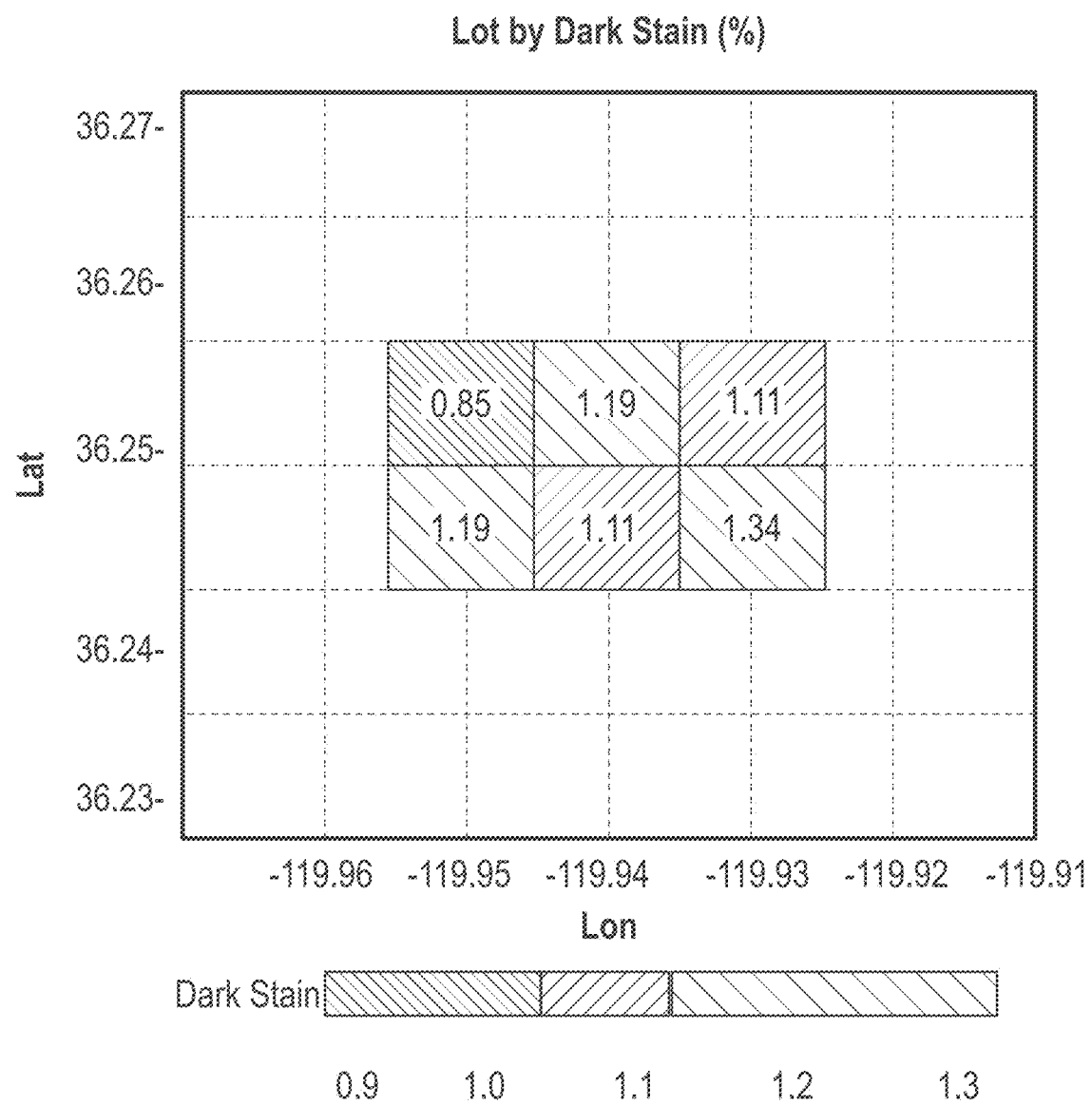
Figure 5D:
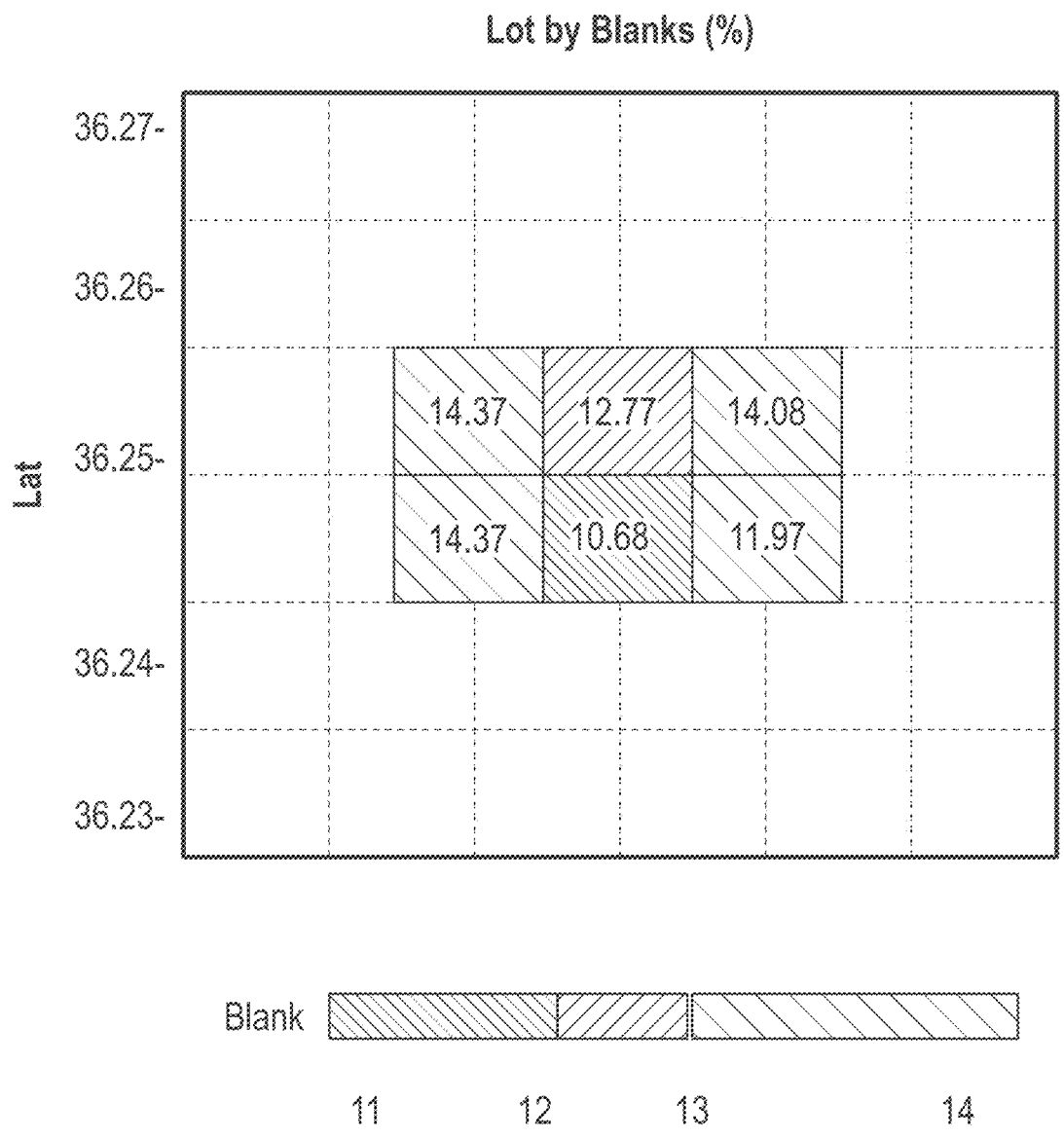
Figure 5E:
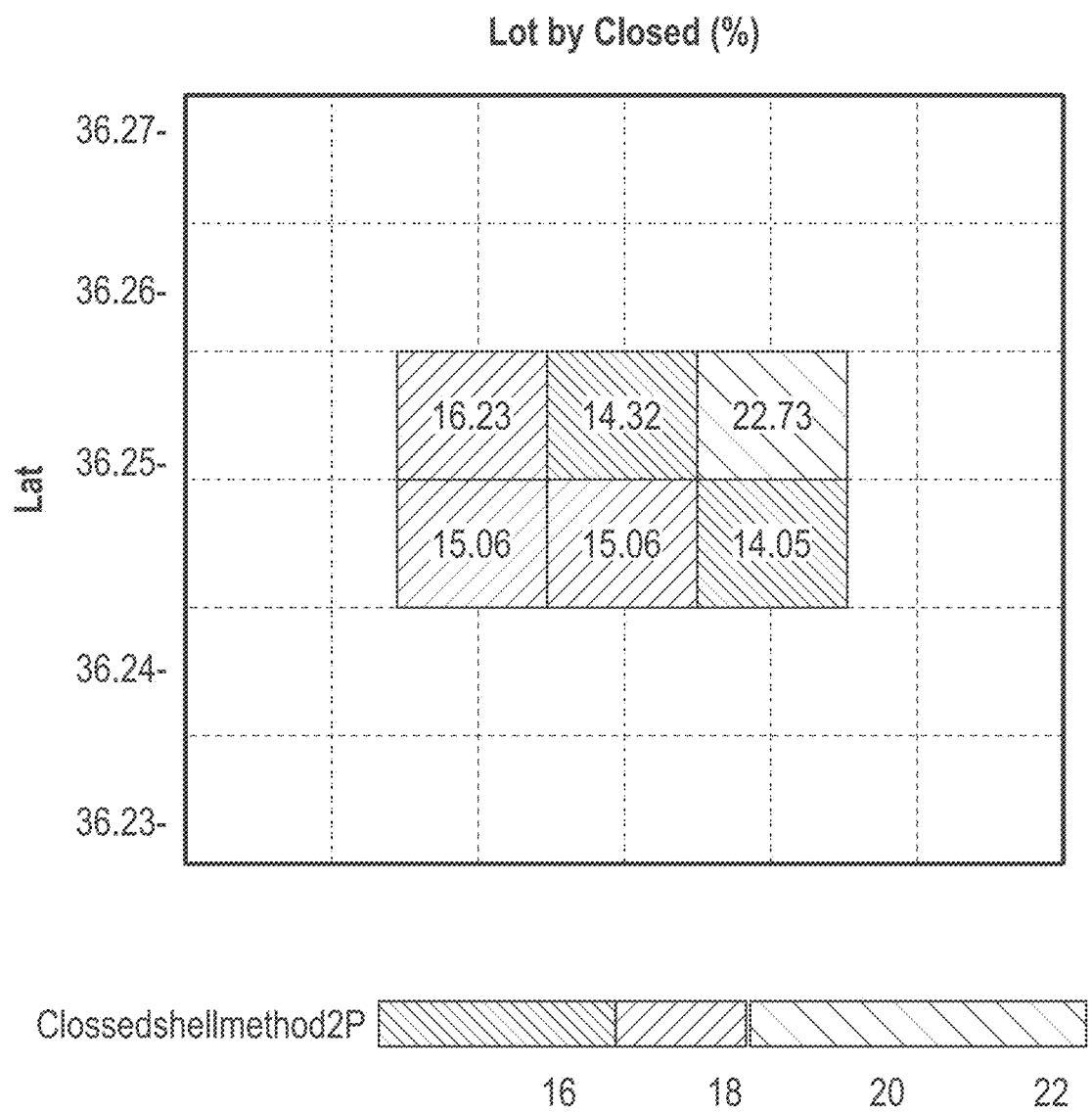
Figure 5F:
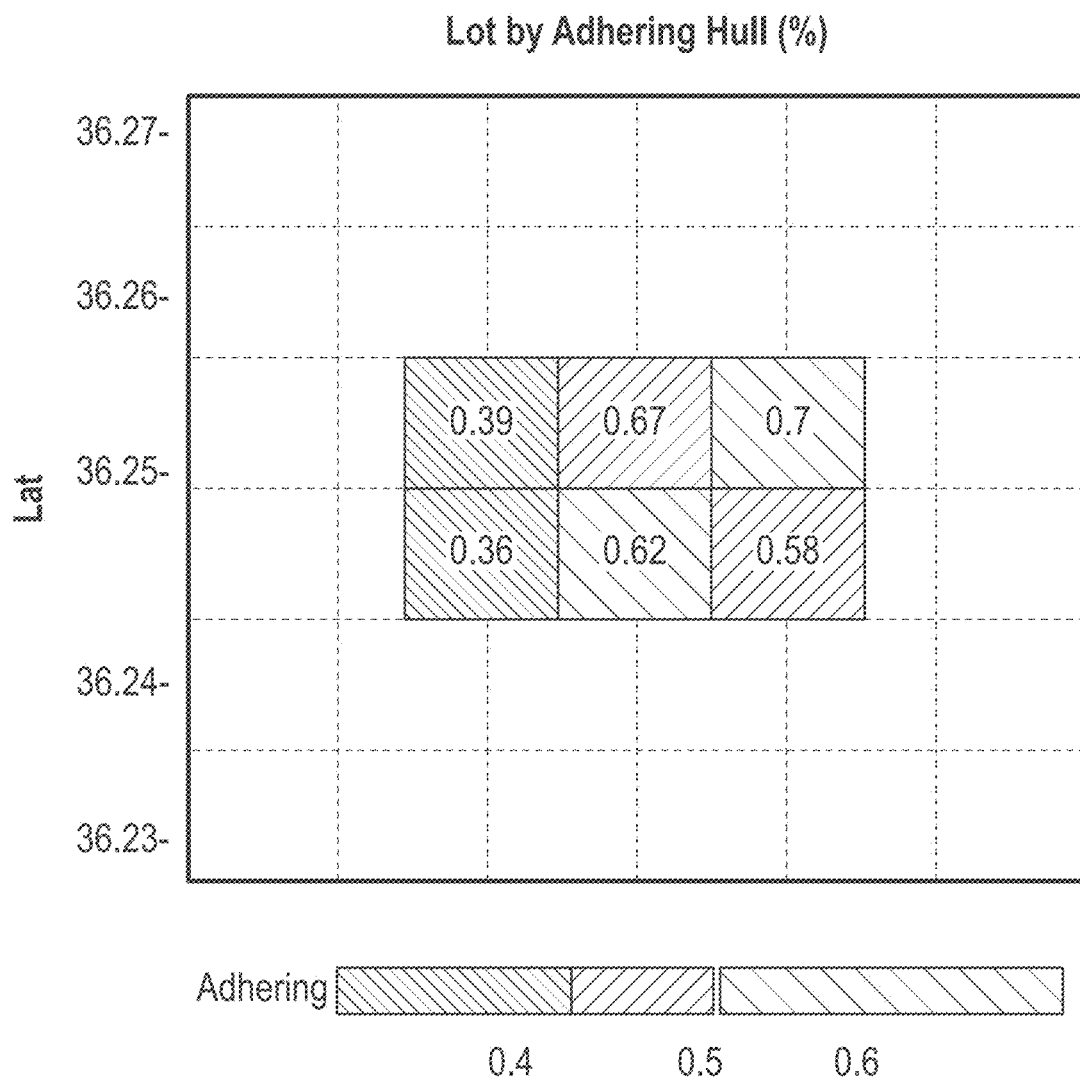

Returning back FIG. 3c, a block diagram illustrating one embodiment for satellite image processing is shown. For this embodiment, image processing 350 receives, as input, satellite spectral data, and generates, as output, a number of spectral indices. Specifically, for this embodiment, image processing 350 generates spectral indices for: normalized difference vegetation index (NDVI), optimized soil adjusted vegetation index (OSAVI), red green ratio index (RGRI), a green normalized difference vegetation index (GNDVI) and a leaf area index (LAI).

Spectral Indices

In one embodiment, the precision agriculture remote sensing platform receives, as input, spectral data (i.e., data generated from reflections of light from the terrain as measured across several spectral bands). In some embodiments, the platform generates several spectral indices. One spectral index is the normalized difference vegetation index (NDVI). The NDVI is a widely used vegetative index in the field of remote agriculture sensing. The NDVI provides a measure of healthy, green vegetation. The index has a sensitivity that allows identification of chlorophyll pigment, so as to provide a useful tool over a broad range of crops and conditions. In general, the NDVI reflects the contrast between the maximum absorption in the red, due to chlorophyll pigments, and the maximum reflection in the infrared band caused by leaf cellular structure. Using the satellite spectral data, the NDVI may be calculated as:

$$NDVI = \frac{(NIR - \text{Red})}{(NIR + \text{Red})}$$

In some embodiments, the precision agriculture remote sensing platform utilizes an optimized soil adjusted vegetation index (OSAVI). The OSAVI provides for greater soil variation than soil adjusted vegetation index (SAW) for low vegetation cover, while demonstrating increased sensitivity to vegetation cover greater than 50%. The OSAVI is best used in areas with relatively sparse vegetation or when soil is visible through the canopy. The OSAVI may be calculated, from the satellite spectral data, using the relationship:

$$OSAVI = \frac{1.5 * (NIR - \text{Red})}{(NIR + \text{Red} + 0.16)}$$

In some embodiments, the precision agriculture remote sensing platform generates a red green ratio index (RGRI). The RGRI provides a ratio expression of leaf redness, caused by anthocyanin, to that of chlorophyll. The RGRI may be used to estimate the course of foliage development in canopies. It is an indicator of leaf production in stress and may also indicate flowering in some canopies. The RGRI may be calculated from the following expression:

$$RGRI = \frac{\sum_{i=600}^{699} R_i}{\sum_{i=500}^{599} R_j}$$

In some embodiments, the precision agriculture remote sensing platform generates, from the satellite spectral data, a green normalized difference vegetation index (GNDVI). Similar to the NDVI, the GNDVI measures the given spectrum from 540 to 570 nanometers, instead of the red spectrum, resulting in greater sensitivity to chlorophyll concentration, than NDVI. The GNDVI may be expressed as:

$$\sqrt[s]{\frac{\sum_{j=1}^{n} W_{i,j} X_j - \bar{X} \sum_{j=1}^{n} W_{i,j}}{\left[n \sum_{j=1}^{n} W_{i,j}^2 - \left(\sum_{j=1}^{n} W_{i,j}\right)^2\right]}{n-1}}$$

In some embodiments, the precision agriculture remote sensing platform further generates a leaf area index (LAI). The LAI may be used to estimate foliar coverage and to forecast crop growth and yield. The exposed area of a leaf to sunlight plays a key role in evapotranspiration. Using the LAI to identify areas of weakness helps elucidate developmental problems as this index defines the area of the crop that intersects with solar radiation. The LAI may be calculated as:

LAI=(3.618*EVI-0.118)>0

Variables

FIG. 8 illustrates one embodiment for some data structures used to define orchard data, satellite data and weather data. For this example embodiment, the partial list of orchard data includes the variables of "tree age", "tree density", "soil data", "quality factor", "yield", "alternate—bearing factor", and "phenology." The column next to the variable name specifies the variable or data type. As shown in FIG. 8, the data type includes both categorical and numerical data types. For example, for the variable "tree age", the data type is "categorical" as the tree age is broken into four different categories (e.g., 0-5, 6-10, 11-25 and greater than 25). The fourth column shown in FIG. 8 identifies the source of the data, such as proprietary (from the orchard owner), public data (USDA) and satellite data. The last column shows a brief explanation of how the data is evaluated, including using a machine-learned model that parses the data into buckets for analysis of subsequent variables. For this embodiment, the satellite data includes the variables "thermal image" and "vegetative index." The weather data includes, for this embodiment, "chilling hours" and "rainfall." Phenology is one variable with a categorical data type. For this variable, the categories include spring, summer, fall and winter.

Figure 9:
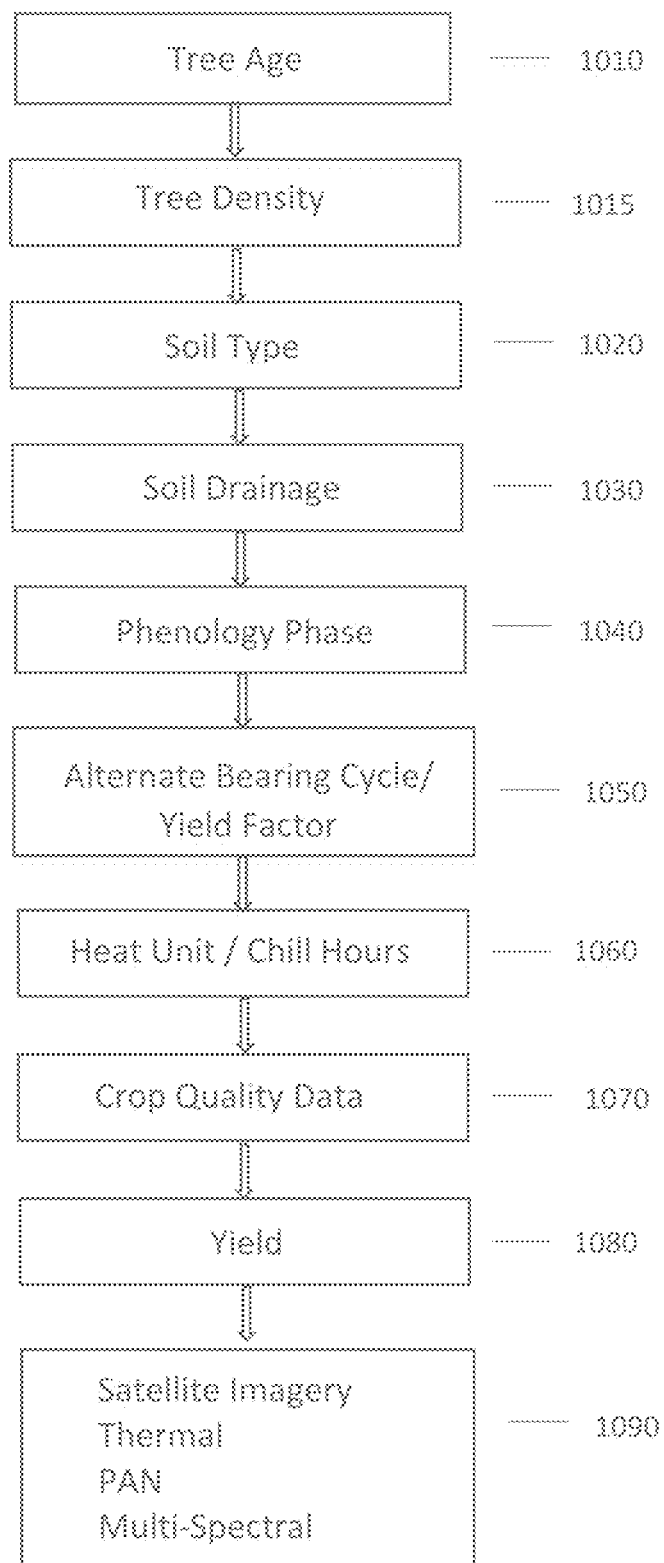
FIG. 9 is a block diagram illustrating one embodiment for evaluating variables in a precision agriculture system to determine output conditions.

FIG. 9 is a block diagram illustrating one embodiment for evaluating variables in a precision agriculture system to determine output conditions. In some embodiments, the variables are processed sequentially (i.e., one variable at a time). As discussed above, data values, associated with a variable, are partitioned into buckets. Subsequently, the next variable is then analyzed on the bucket assigned from the previous variable. FIG. 9 represents one embodiment for an order or priority to process the variables for evaluating orchard and satellite data. For this embodiment, the precision agriculture system evaluates, in this order, "tree age" (1010), "tree density" (1015), "soil type" (1020), "soil drainage" (1030), "phenology phase" (1040), "alternate-bearing cycle/yield factor" (1050), "heat unit/chilling hours" (1060), "crop quality data" (1070) and "yield" (1080). In addition to the variables for orchard data (and external weather data), the variables for satellite imagery are shown in the last stage of the evaluation. Specifically, satellite imagery is analyzed to determine the variables "thermal", "PAN", and "multispectral" (1090).

Orchard Data Model

Figure 10:
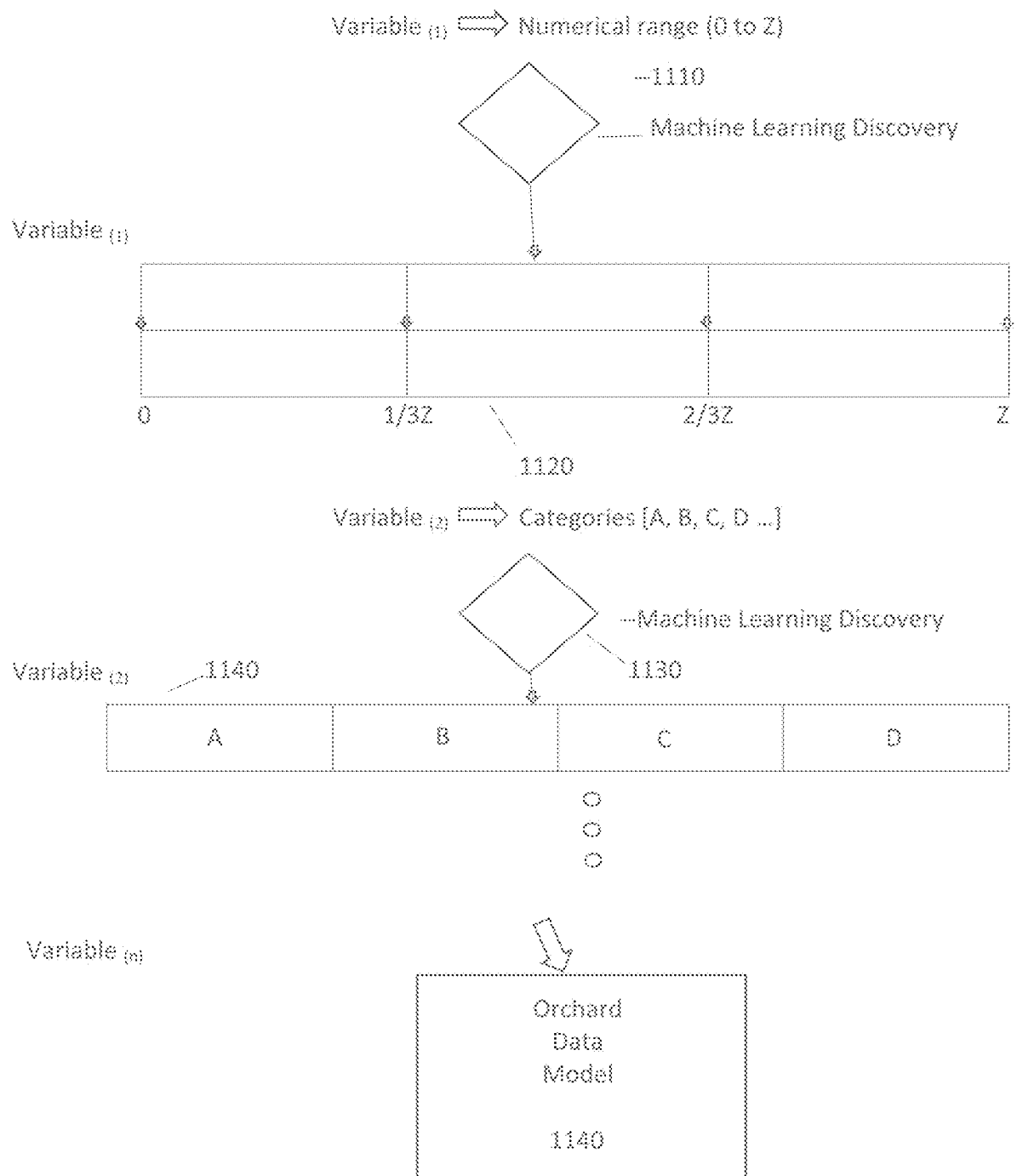
FIG. 10 is a block diagram illustrating a process to create the orchard data model in accordance with one embodiment.

In some embodiments, the orchard data model consists of a hierarchy of variables which, when delineated into buckets, form pathways that provide correlations among the variables to one or more output metrics. FIG. 10 is a block diagram illustrating a process to create the orchard data model in accordance with one embodiment. As discussed in FIG. 8, the variables for the orchard data model have several different data types. For example, in one embodiment, the data types include "categorical" and "numerical" for both orchard and external data. For the example shown in FIG. 10, the first variable, variable$_{(1)}$, has a numeric range from "0 to Z." Using a machine learning process, during a first stage of discovery, boundaries of values for the variables are delineated to create buckets or pathways for optimizing the predictions of the output conditions. As illustrated in FIG. 10, using machine learning discovery, variable$_{(1)}$ is demarcated into three buckets: 0 to ⅓Z, ⅓Z to ⅔Z, and ⅔Z to Z. Specific values for numeric ranges used in variables are discussed more fully below in conjunction with FIGS. 13(*a*) and 13(*b*).

For the example of FIG. 10, a second variable, variable$_{(2)}$, has a categorical data type (categories A, B, C, D . . . ). Similar to variable$_{(1)}$, machine learning techniques are used to discover boundaries of variable$_{(2)}$ that demarcate buckets or pathways based on the different categories of the variable. This process continues for all of the variables (up to variable $_{(n)}$) to discover pathways and create buckets in order to develop a first stage model for the orchard data model (1140). Specifically, the discovery process determines how the values of the variable influence the output predictor (e.g., anomaly predictor). For example, in one embodiment, machine learning determines that the boundaries for the values for the tree age variable are (0-5), (6-10), (11-25), and (greater than 25). This demarcation for tree age reveals that trees in these age brackets may be analyzed similarly (i.e., new trees aged 0 to 5 have similar age related characteristics for analysis in the model). The chilling hours variable, also with a numerical data type, was discovered to have an effective delineation of buckets that consist of less than 800, 801-900, 900-1,000 and greater than 1,000.

Figure 11:
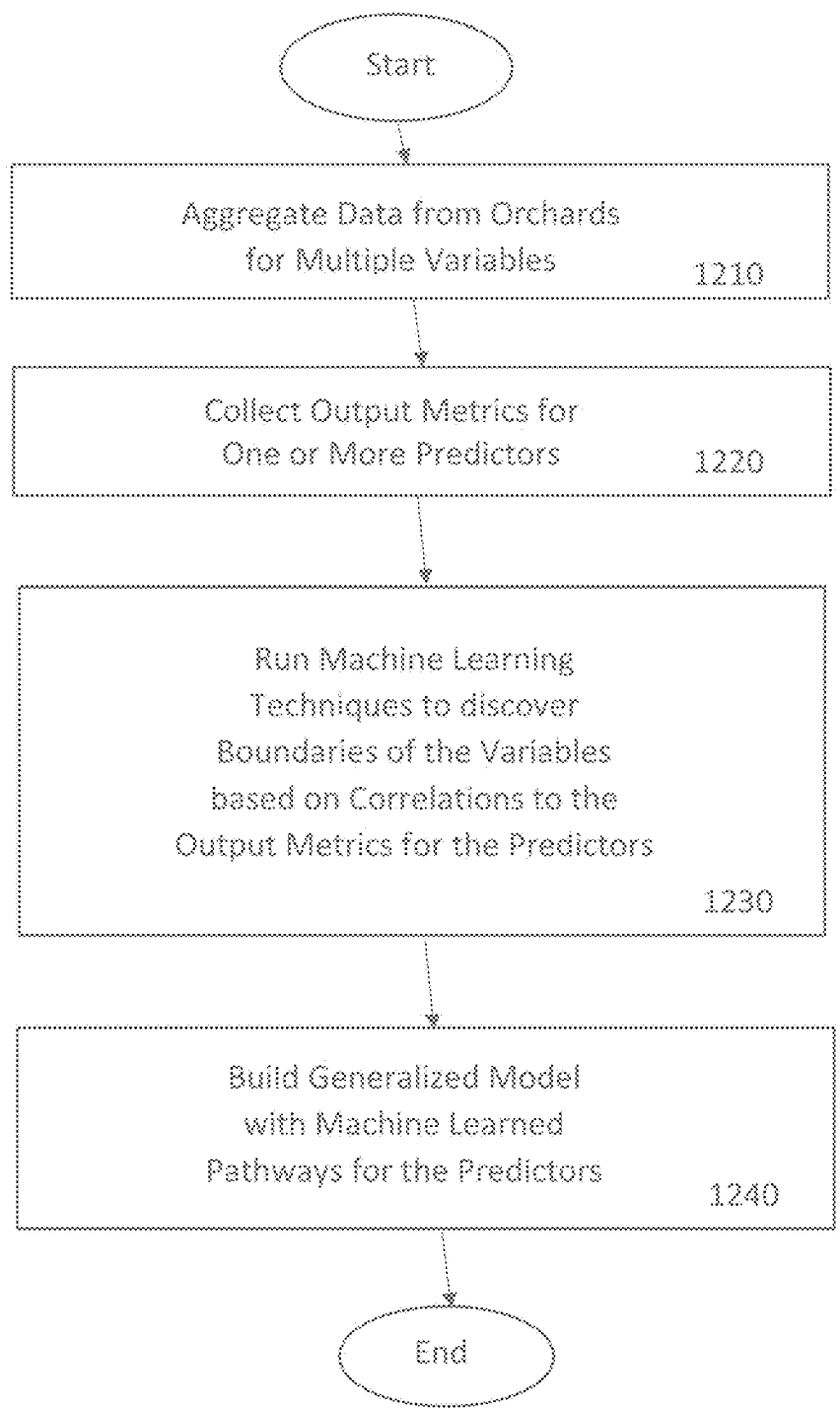
FIG. 11 is a flow diagram illustrating one embodiment for discovering boundaries and variables for creating pathways or buckets in an orchard data model.

FIG. 11 is a flow diagram illustrating one embodiment for discovering boundaries and variables for creating pathways or buckets in an orchard data model. Data from one or more orchards are aggregated for multiple variables (e.g., tree age, tree density, soil, chilling hours, etc.) (Block 1210). Output metrics are collected for one or more predictors (block 1220). The output metrics comprise observed conditions that relate to the output conditions (i.e., output conditions predicted by the model). For example, for the output condition "disease detected", the output metrics may include characteristics, observed on the trees, fruit or soil, associated with known disease problems, such as wilt. To create a first stage for the orchard data model, machine-learning techniques are run to discover boundaries of the variables based on the correlations of the variable values to the output metrics for the predictors (block 1230). For example, for the "disease detected" output predictor, the first stage training phase correlates ranges within the variables, such as tree density ranges, based on the output metrics (e.g., diseased orchards). Any machine-learning techniques, such as machine learning techniques that use various types of machine-learning algorithms (e.g., nonlinear regression, linear regression, etc.) may be used to establish the relationships between the input variables and the output metrics without deviating from the spirit and scope of the invention.

Figure 12:
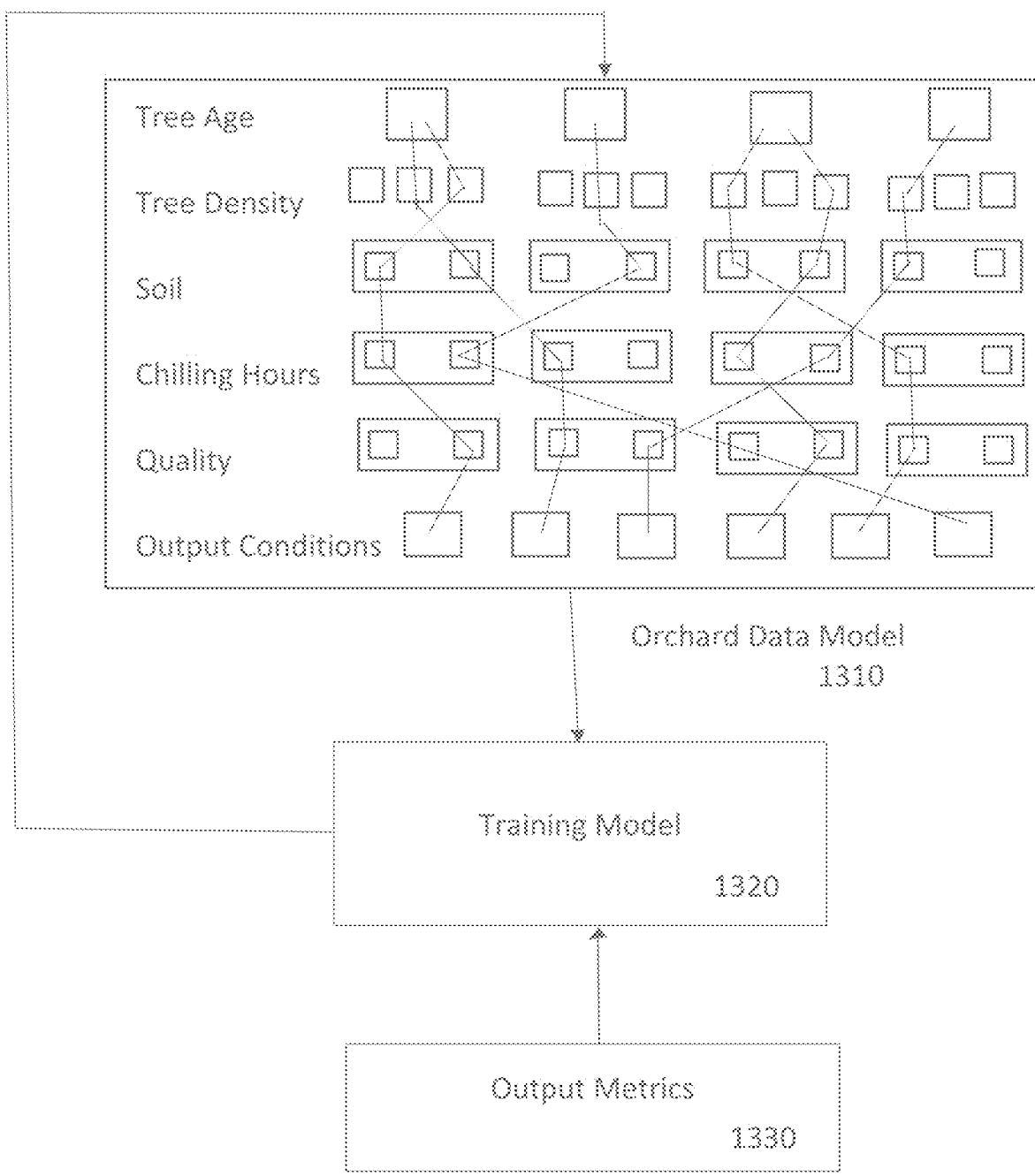
FIG. 12 is a block diagram illustrating one embodiment for generating the orchard data model through a second machine learning stage.

FIG. 12 is a block diagram illustrating one embodiment for generating the orchard data model through a second machine learning stage. A computer platform is used to create the orchard data model. Orchard data model 1310 includes a number of variables, each variable is partitioned into buckets. For the specific embodiment of FIG. 12, the variables of tree age, tree density, soil, chilling hours, and quality are partitioned into preliminary pathways discovered in the first machine learning stage. The lines shown in FIG. 12 connect the buckets in orchard data model 1310 to create exemplary pathways discovered in the first machine learning stage. The paths shown in FIG. 12 are only illustrative of a concept, such as the concept of learned pathways through nodes of a neural network, and are not to be construed as actual paths discovered in an implementation. The orchard data model 1310 is run against a training model (per orchard) 1320. During the second machine learning stage, the layers of variables are further correlated to the output metrics 1330. In essence, the output metrics 1330 calibrate the orchard data model to the output conditions. In some embodiments, the output metrics 1330 may be an observed condition at the orchard, such as the observed conditions of disease, water leak, soil problems, etc. Since the data for the variables and the output metrics are specific to an orchard, the second machine learning stage builds an orchard data model specific to each orchard (i.e., each orchard has a unique signature due to its unique characteristics). Any machine-learning techniques, such as machine learning techniques that use various types of machine-learning algorithms (e.g., nonlinear regression, linear regression, etc.) may be used to establish the relationships between the buckets of input variables and the output metrics for the second machine learning stage without deviating from the spirit and scope of the invention.

Figure 13A:
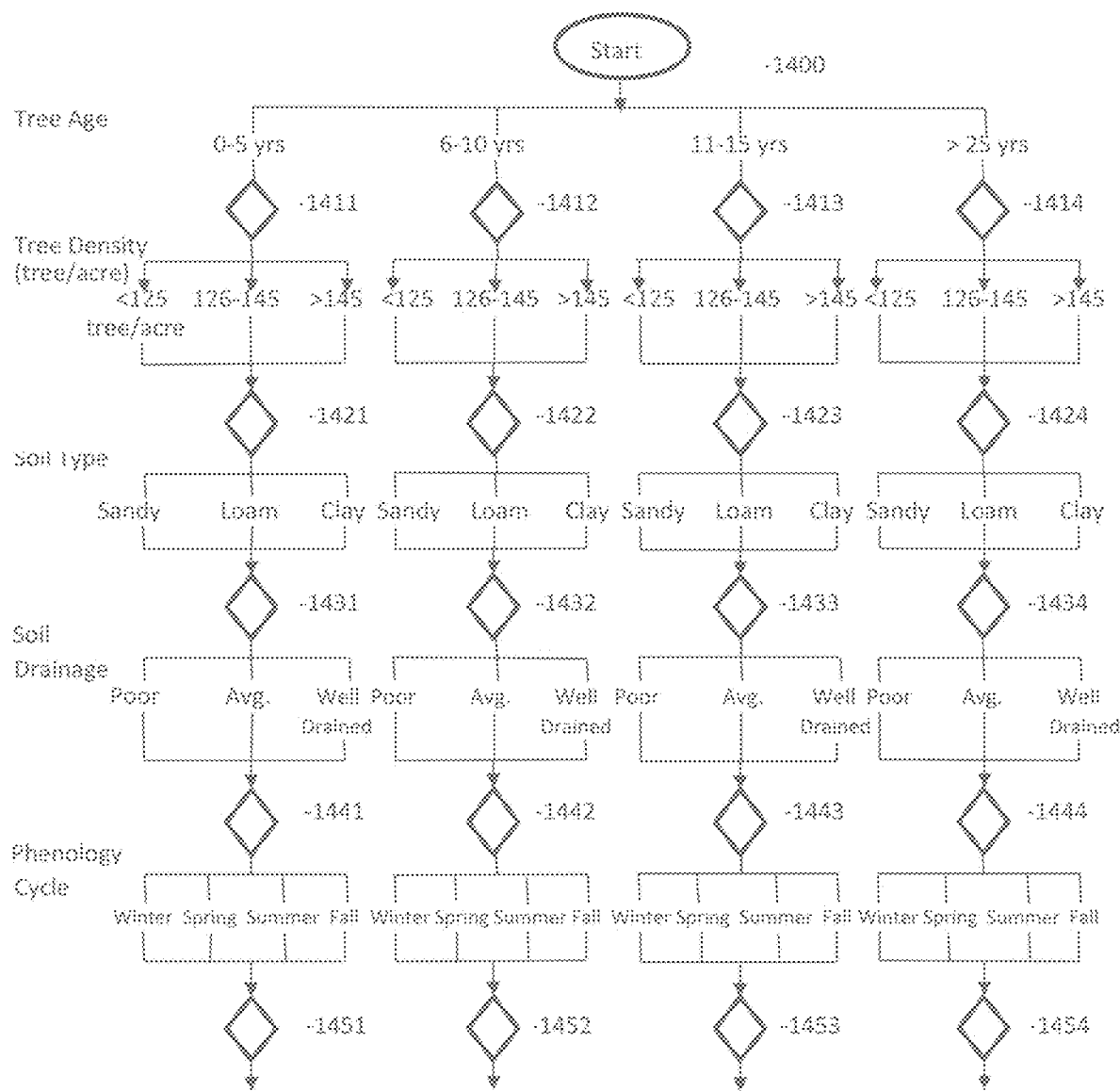
FIGS. 13(a) and (b) is a block diagram illustrating one embodiment for a trained orchard data model.
Figure 13B:
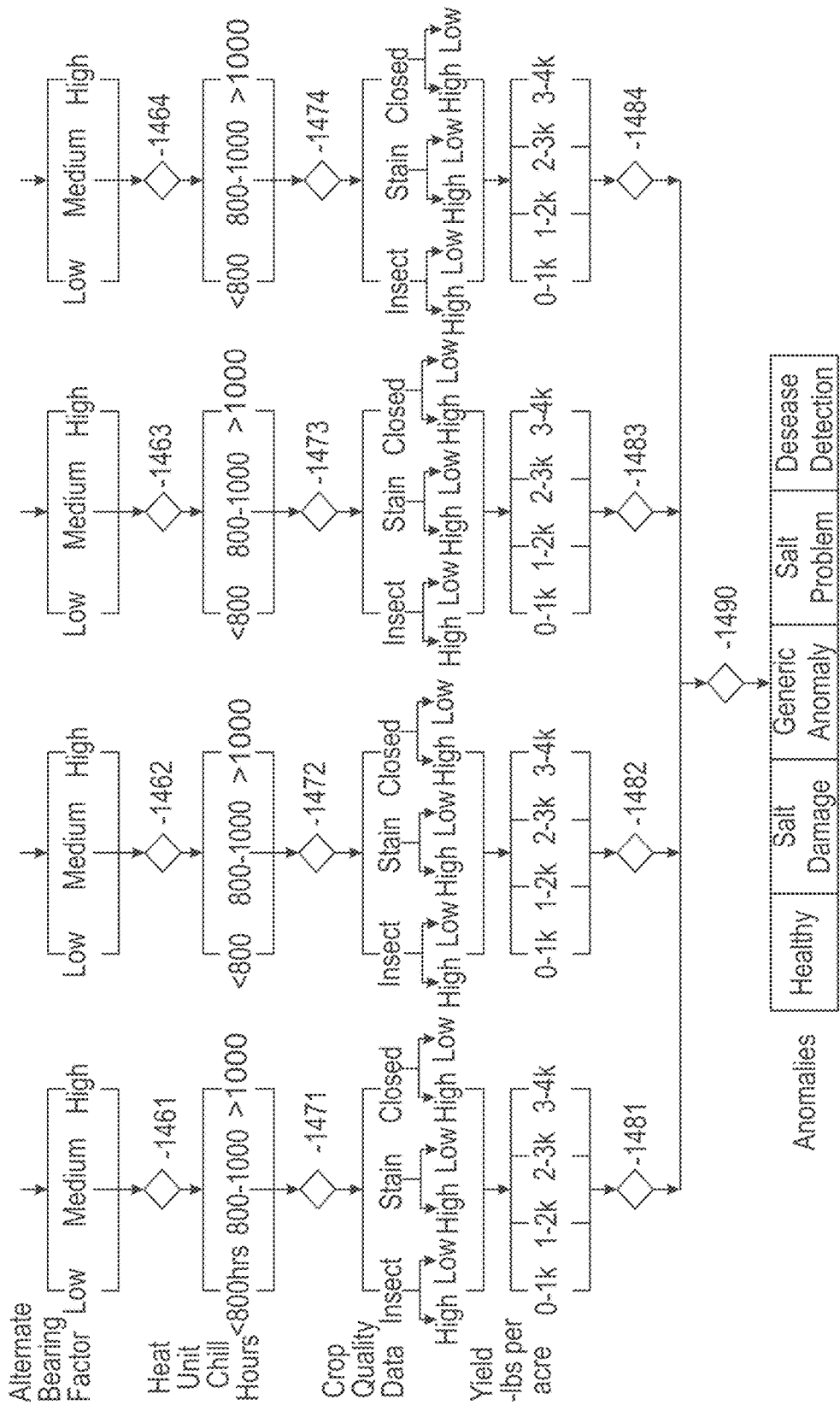

FIGS. 13*a* and 13*b* is a block diagram illustrating one embodiment for a trained orchard data model. For this embodiment, several variables are trained to assess the output conditions in orchard data model 1400. Specifically, the variables of tree age, tree density, soil, chilling hours and quality are used to predict the output conditions of water leak, salt damage, generic anomaly, soil problem and disease detected. As discussed above, during the first machine learning stage, the machine-learning techniques discover the boundaries for the variables to demarcate the variables into buckets. For the example of FIG. 13, tree age was divided into the buckets of 0 to 5 years, 6-10 years, 11-25 years and greater than 25 years. For this example, the second variable, tree density, was partitioned into three buckets: less than 125 trees per acre, 126-145 trees per acre, and greater than 145 trees per acre. The soil type variable, a categorical data type, is classified as "sandy", "loam", and "clay." The fourth variable shown on FIG. 13, soil drainage includes, for this embodiment, the categories "poor", "average" and well-drained." The fifth variable, which defines the phenology cycle of the trees, comprises the categories of "winter", "spring", "summer" and "fall."

The alternate bearing factor is the sixth variable shown in FIG. 13. The alternate bearing factor is a measure of how much energy the tree exerted in the past as evidenced by the crop output. The alternate bearing factor, for this embodiment, includes the categories of "low", "medium" and "high." The seventh variable, heat unit/chilling hours, includes the relevant boundaries of less than 800 hours, 801-1000 hours, and greater than 1000 hours. The eighth variable shown in FIG. 13 is crop quality data (i.e., quality of the fruit produced). For this example, the crop quality data variable includes a data structure that identifies both a quality metric (insect, stained, and closed mouth) as well as a quantitative assessment of each quality indicator (e.g., high or low). The last variable shown in the embodiment of FIG. 13 is the yield variable, expressed in pounds per acre, that specifies ranges of yields for orchards. Specifically, for this embodiment, the ranges are "0-1K", "1K-2K", "2K-3K", "3K-4K."

The orchard data model 1400, shown in FIG. 13, include a number of decision elements (i.e., 1411, 1412, 1413, 1421, 1422, 1423, 1431, 1432, 1433, 1441, 1442, 1443 and 1450). These decision elements create the pathways of the model (learned pathways) based on the orchard data specific to the orchard. For this embodiment, the orchard data model 1400 generates predictions for the output conditions of healthy vegetation, salt damage, soil problem, generic anomalies and disease detected.

Satellite Data Model

Figure 14A:
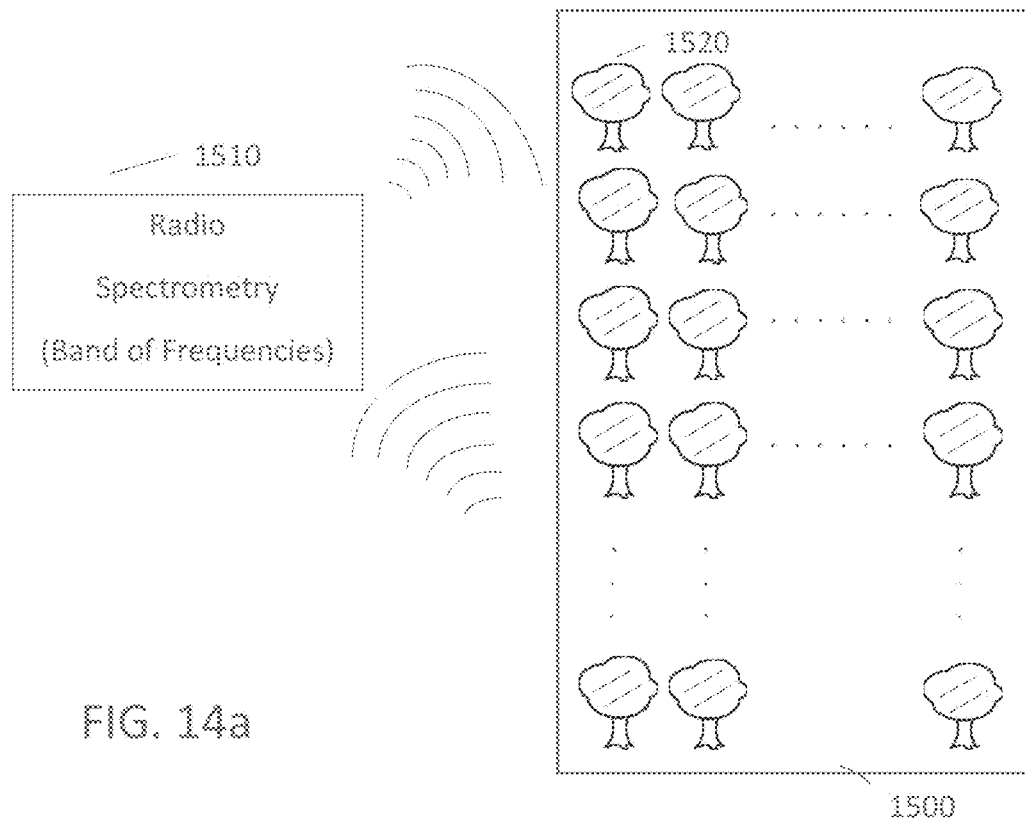
FIG. 14(a) is a block diagram illustrating one embodiment to generate a satellite model for integration into a precision agriculture system.
Figure 14B:
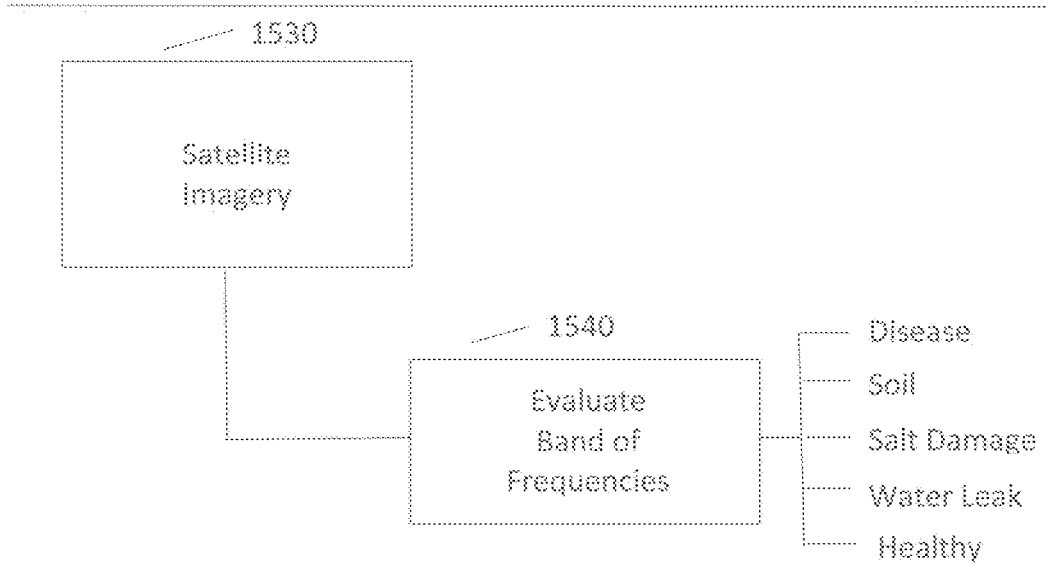
FIG. 14(b) depicts a block diagram for processing satellite imagery to identify characteristics through previously identified bands of frequencies discovered from the process depicted in FIG. 14(a).

FIG. 14(*a*) is a block diagram illustrating one embodiment to generate a satellite model for integration into a precision agriculture system. For this embodiment, a two-step process is used. First, satellite image information is collected and spectral indices are calculated. Then, the satellite images are analyzed to detect spectrum(s) of frequencies and to interpret the spectral indices to detect one or more output conditions. In one embodiment, a radio spectrometry system (1510) is used to gather reflectance information for one or more attributes or qualities of the orchard (1500). Specifically, radio spectrometry equipment 1510 is co-located, such as at orchard 1500. Then, characteristics of one or more attributes or qualities of the orchard (1500), such as standing water, are identified. The radio spectrometry equipment 1510 is used to transmit and then gather reflected bands of frequencies that capture the desired attributes or qualities of the orchard (1500). For example, if the attribute is soil (e.g., differentiate soil from trees), then the radio spectrometry 1510 identifies a band of frequencies that identify soil only. A description of various characteristics, attributes or qualities observed and recorded in the orchards is described more fully below in conjunction with FIGS. 15(*a*)-(*e*).

FIG. 14(*b*) depicts a block diagram for processing satellite imagery to identify characteristics through previously identified bands of frequencies discovered from the process depicted in FIG. 14(*a*). For this example, satellite imagery (1530) is input to a processing block (1540) to evaluate and track the bands of frequencies discovered in the field calibration experiments. A computer platform is used to evaluate the band of frequencies 1540. For this example, the precision agriculture system evaluates frequencies to detect disease, soil, salt damage, water leak, generic anomalies and healthy vegetation.

FIG. 15(*a*) depicts using field equipment to gather bands of wavelengths associated with disease crops. For this application, orchard 1612 includes samples and examples of diseased trees (1620 and 1630). The disease of the tree may be identified as a particular known condition, such as Verticilium Wilt 1640, or have an appearance of a general but non-identified disease condition. The radio spectrometer 1608 transmits energy to the example diseased trees, and records the bands of reflectance for the various disease conditions as disease bands of wavelengths 1610.

Figure 16:
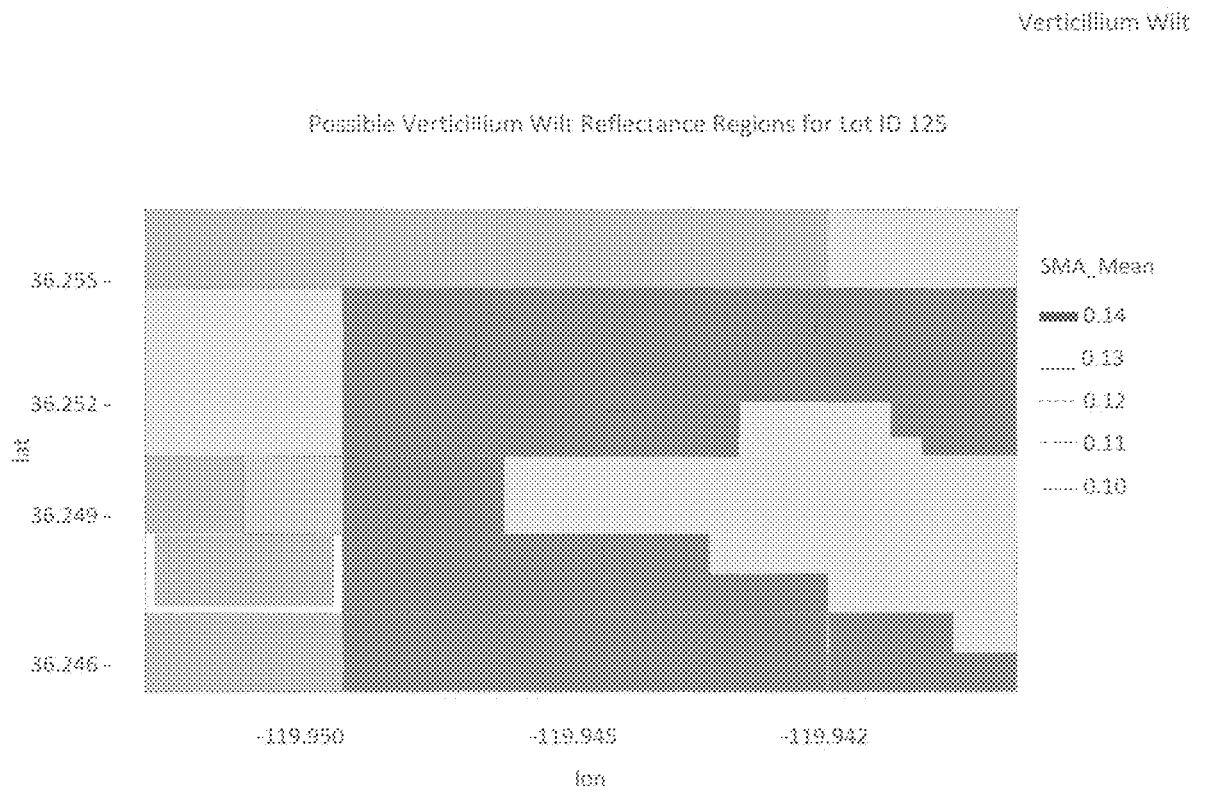

FIG. 16 depicts a satellite image for an example orchard lot that highlights possible Verticillium Wilt reflectance regions. As shown in FIG. 16, the correlation of the bands of frequencies in the satellite image to the healthy vegetation reflectance regions are plotted, including how the satellite image for the orchard compares with disease reflectance regions.

The different gray scales shown correlate to the SMA Mean chart to show the level of comparison between the satellite image and the detected Verticillium Wilt reflectance regions.

FIG. 15(*b*) depicts a process to generate healthy bands of wavelengths reflected from healthy orchards. Orchard 1648 has multiple samples of healthy trees (1650, 1655 and 1660). Trees may be characterized as healthy trees from multiple characteristics or qualities of the tree, including quality of the crop and appearance characteristics of the tree for known healthy characteristics. Radio spectrometry 1643 emits energy to orchard 1648, captures reflectance bands for conditions associated with the sample healthy trees to create the healthy bands of wavelengths 1645.

Figure 17:
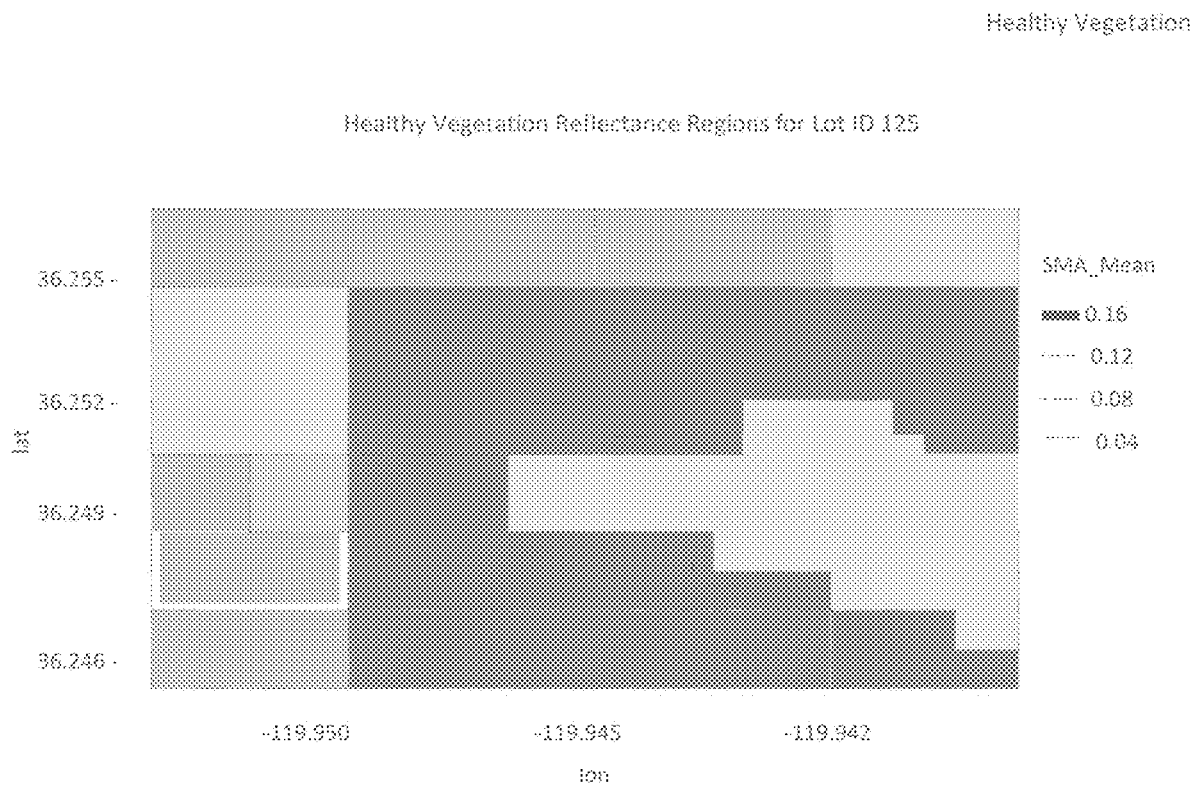
FIG. 17 depicts a satellite image for an example orchard lot that highlights healthy vegetation reflectance regions.

FIG. 17 depicts a satellite image for an example orchard lot that highlights healthy vegetation reflectance regions. As shown in FIG. 17, the correlation of the bands of frequencies in the satellite image to the healthy vegetation reflectance regions are plotted, including how the satellite image for the orchard compares with healthy vegetation reflectance regions. The different gray scales shown correlate to the SMA_Mean chart to show the level of comparison between the satellite image and the detected healthy vegetation reflectance regions.

FIG. 15(*c*) illustrates a process to collect soil bands of wavelengths for use in the precision agriculture system. For this process, several soil conditions adversely affecting the orchards are identified. Radio spectrometry 1663, co-located with orchard 1668, transmits energy, and records the soil bands of wavelengths 1670 by associating the reflectance bands of wavelengths with soil conditions. The bands of wavelengths may include a band of wavelengths used to specifically identify salt damage (1665). The soil condition may be a specific condition, such as salt damage 1676, or it may be a generalized condition identified as a soil anomaly (1672 and 1674).

Figure 18:
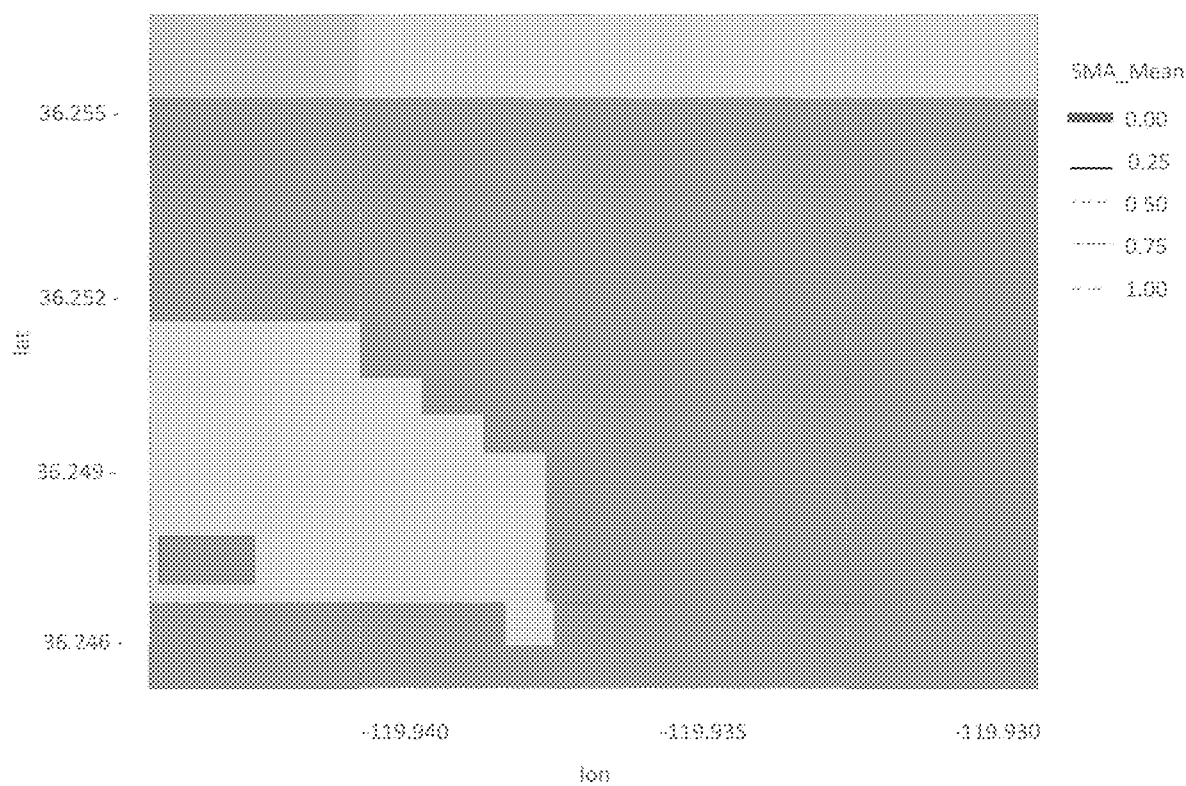
FIG. 18 depicts a satellite image for an example orchard lot that highlights possible salt damaged reflectance regions.

FIG. 18 depicts a satellite image for an example orchard lot that highlights possible salt damaged reflectance regions. As shown in FIG. 18, the correlation of the bands of frequencies in the satellite image to the possible salt damaged reflectance regions are plotted, including how the satellite image for the orchard compares with possible salt damaged reflectance regions. The different gray scales shown correlate to the SMA_Mean chart to show the level of comparison between the satellite image and the detected possible salt damaged reflectance regions.

Figure 19:
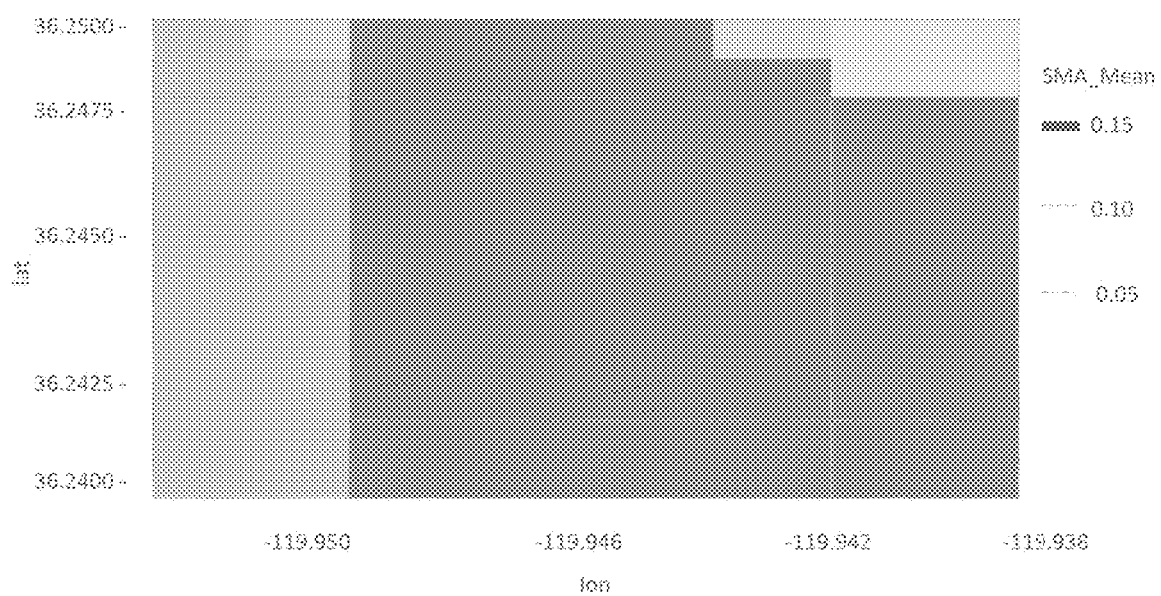
FIG. 19 depicts a satellite image for an example orchard lot that highlights soil reflectance regions.

FIG. 19 depicts a satellite image for an example orchard lot that highlights soil reflectance regions. As shown in FIG. 19, the correlation of the bands of frequencies in the satellite image to the soil reflectance regions are plotted, including how the satellite image for the orchard compares with soil reflectance regions. The different gray scales shown correlate to the SMA Mean chart to show the level of comparison between the satellite image and the soil reflectance regions.

Figure 15A:
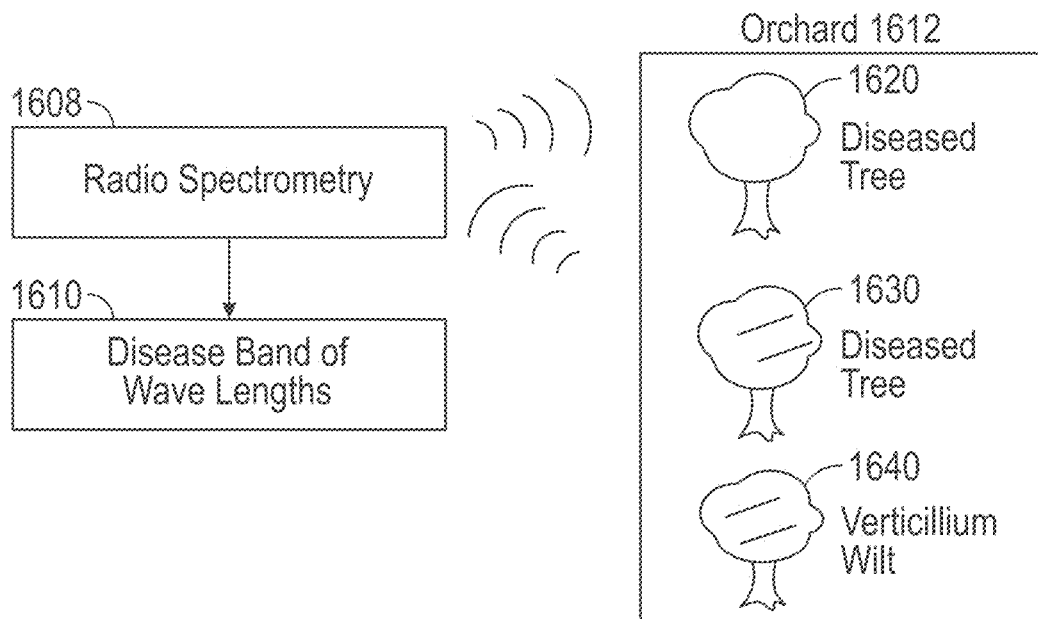
FIG. 15(a) depicts using field equipment to gather bands of wavelengths associated with disease crops.
Figure 15B:
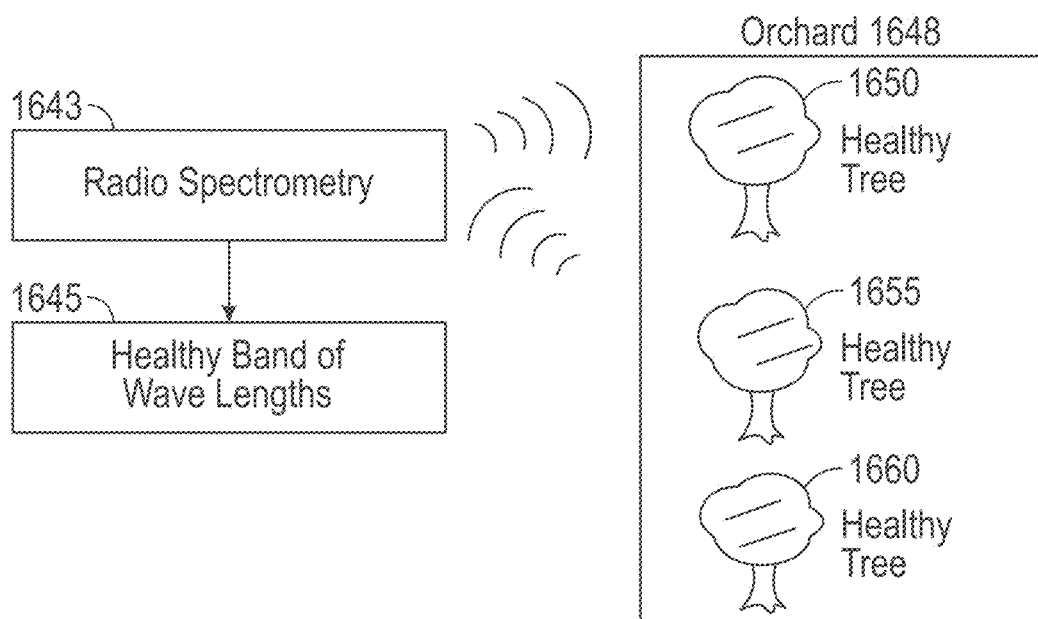
FIG. 15(b) depicts a process to generate healthy bands of wavelengths reflected from healthy orchards.
Figure 15C:
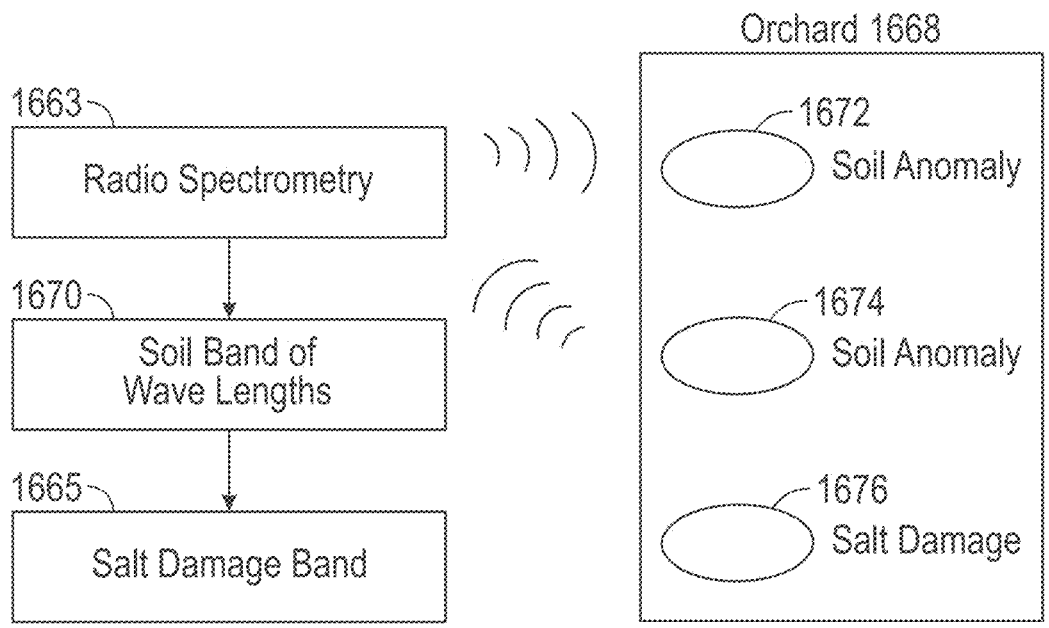
FIG. 15(c) illustrates a process to collect soil bands of wavelengths for use in the precision agriculture system.
Figure 15D:
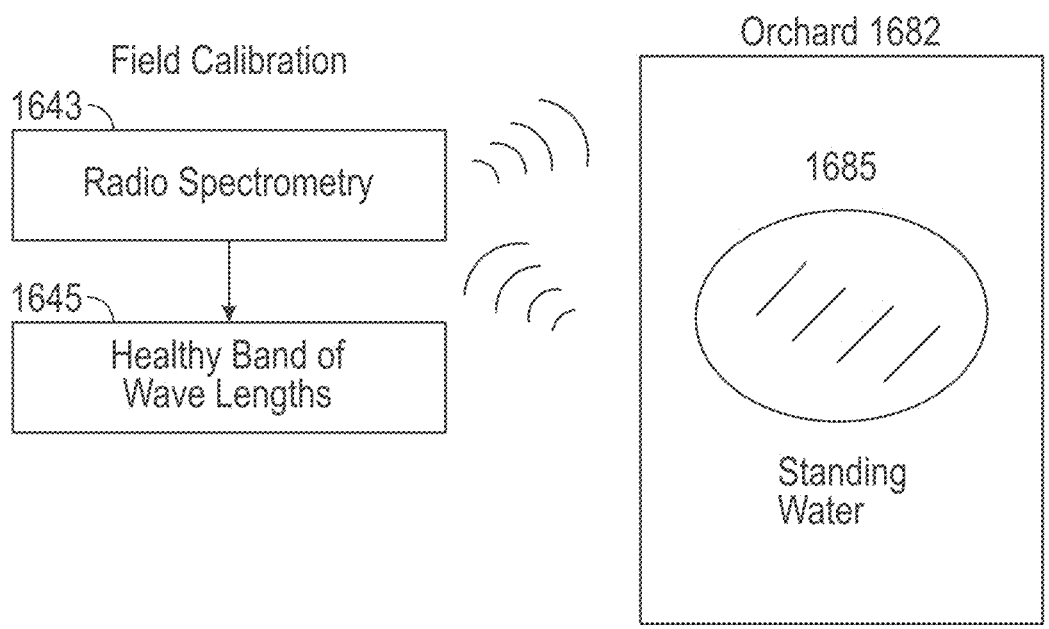
FIG. 15(d) illustrates a field calibration process to acquire a band of frequencies that detect water leak.

FIG. 15(d) illustrates a field calibration process to acquire a band of frequencies that detect water leak. To calibrate the water leak output condition, standing water (1685) is identified in orchard 1682. Radio spectrometry 16788 emits the energy and records the reflectance of bands of frequencies that identify the standing water to generate the water leak band of frequencies 1680.

Figure 15E:
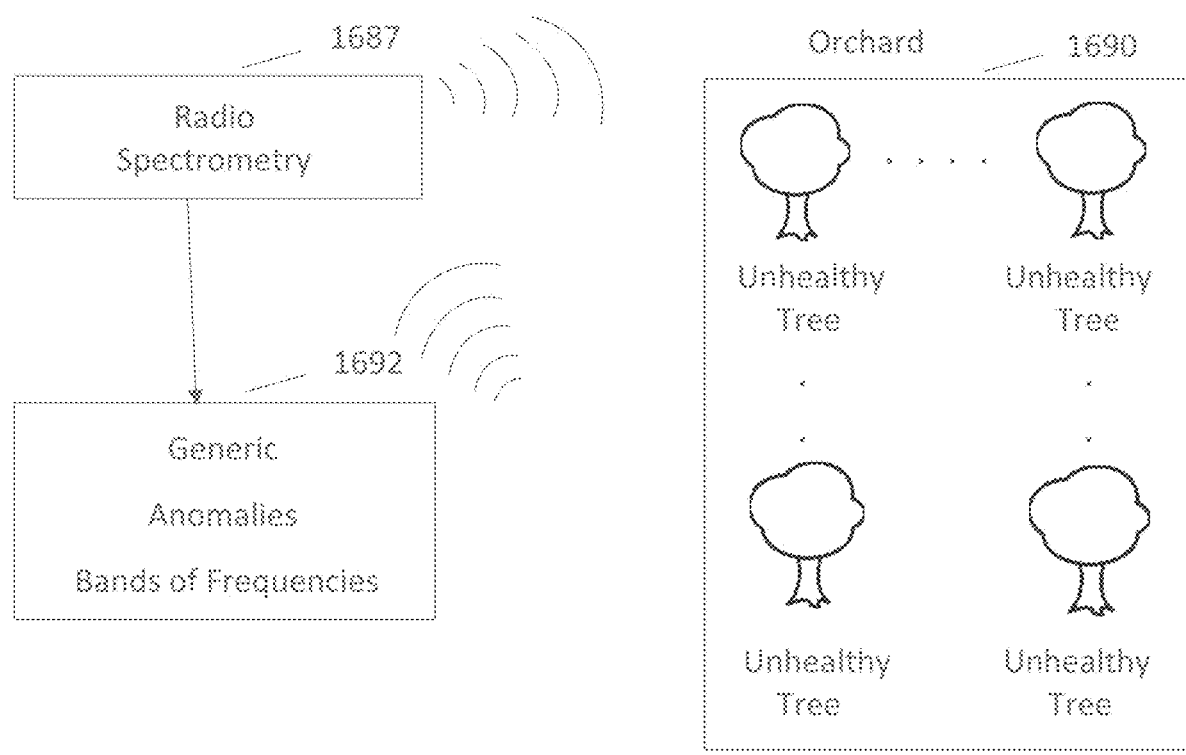
FIG. 15(e) depicts a process to generate bands of frequencies that identify generic anomalies in orchards.

FIG. 15(e) depicts a process to generate bands of frequencies that identify generic anomalies in orchards. To calibrate these bands of frequencies for use in the precision agriculture system, unhealthy trees are identified in orchard 1690. An unhealthy tree is a tree that exhibits any number of characteristics that indicate poor health. The observed characteristic may be identifiable as having a root cause or the characteristic may generally reflect a tree in poor health without an identified cause. Radio spectrometry 1687, co-located with orchard 1690, transmits energy and captures the reflectance of bands of frequencies associated with the observed characteristics in unhealthy trees to generate bands of frequencies for generic anomalies 1692.

Generic anomalies may also be calculated from spectral indices. In some embodiments, the precision agriculture system calculates leaf area index (LAI) to determine the surface area of the leaf exposed upward, and therefore the angle of the leaf relative to the sun in the sky above. The leaves of a healthy tree will track the movement of the sun as the sun moves across the sky during the day. The precision agriculture system samples the LAI several times during the day in order to track the orientation of the leaf to the sky. In some embodiments, the precision agriculture system compares LAIs from different tress to determine whether the movement of the leaves is fairly consistent among the tress. If any trees do not possess LAIs as other tress in the orchard, then those trees are flagged as a generic anomaly.

Figure 20:
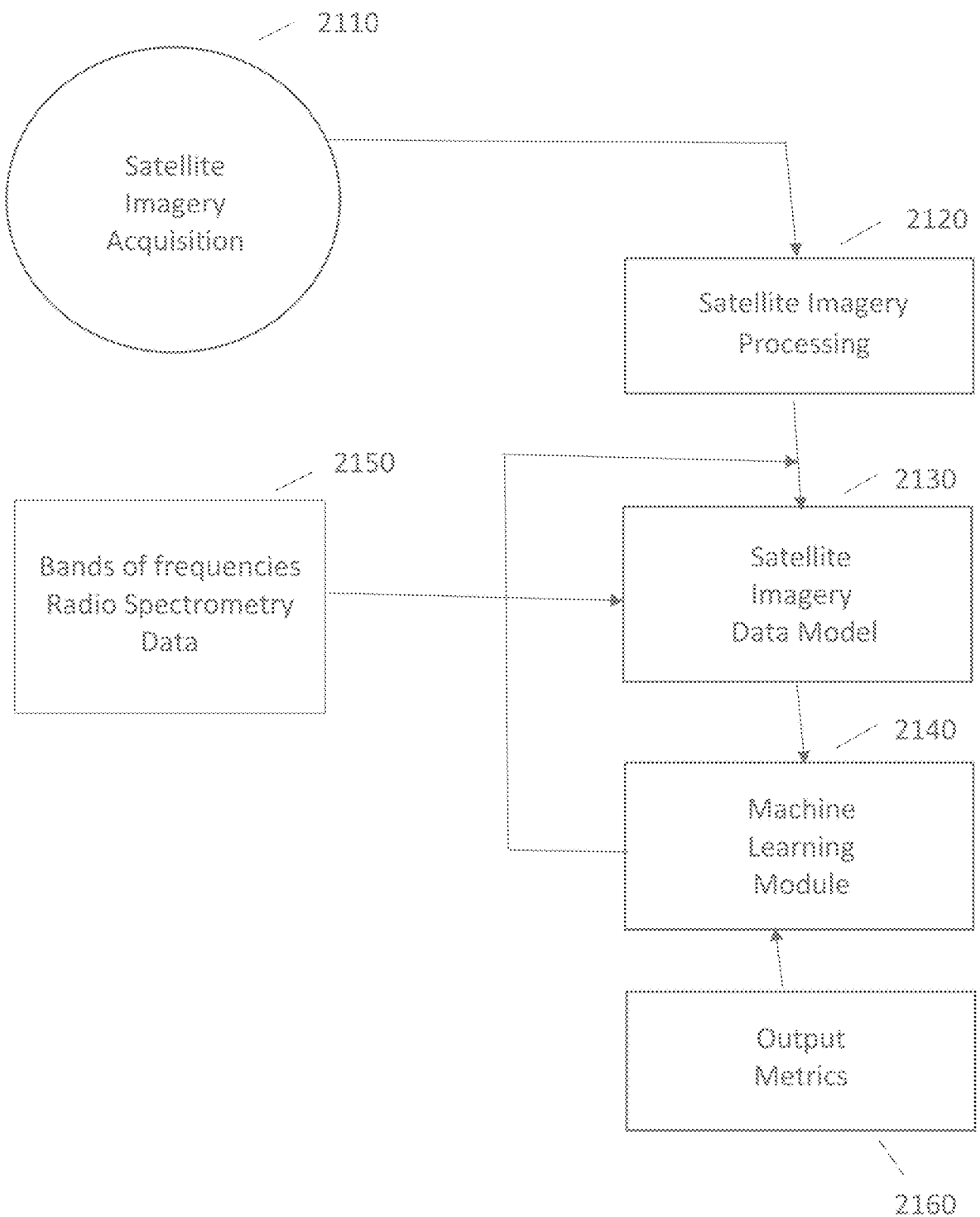
FIG. 20 illustrates a system for generating a satellite image model in accordance with one embodiment for the precision agriculture system of the present invention.

FIG. 20 illustrates a system for generating a satellite image model in accordance with one embodiment for the precision agriculture system of the present invention. As discussed above, satellite images are received (satellite imagery acquisition 2110) for intermediate processing in satellite image processing (2120) to generate spectral indices. The spectral indices are input to the satellite imagery data model to detect various output conditions (e.g., water leak, healthy vegetation, soil detection, generic anomalies, disease detection, etc.). Also, as discussed above, bands of frequencies, obtained from the field studies, are determined to detect the various output conditions. Satellite imagery data model 2130 receives, as inputs, processed satellite images from satellite imagery processing 2120 and the bands of frequencies for the output conditions (2150). The satellite imagery data model is trained to predict the output conditions from the processed satellite imagery based on spectral indices, bands of frequencies (2150) and the output metrics (2160). As shown in FIG. 20, for this embodiment, machine-learning module (2140) uses a machine-learning algorithm (e.g., nonlinear regression, linear regression, etc.) to correlate the processed satellite imagery (spectral indices) and the bands of frequencies (2150) to the output metrics (2160). The machine-learning module (2140) also validates, and calibrates as necessary, paths to determine the output conditions from the band of frequencies (radio spectrometry data) with paths that interpret the spectral indices to determine output conditions. The output metrics provide the observed characteristics at the orchard that correspond to the output conditions (e.g., water leak, healthy vegetation, soil detection, generic anomalies, disease detection, etc.). As is recognized in the art of computing, various training techniques, such as training techniques that use training data sets, and machine learning algorithms (e.g., nonlinear regression, linear regression, etc.) may be used to train the satellite imagery data model to extract the bands of frequencies from the processed satellite imagery to predict one or more output conditions, without deviating from the spirit or scope of the invention.

Figure 21:
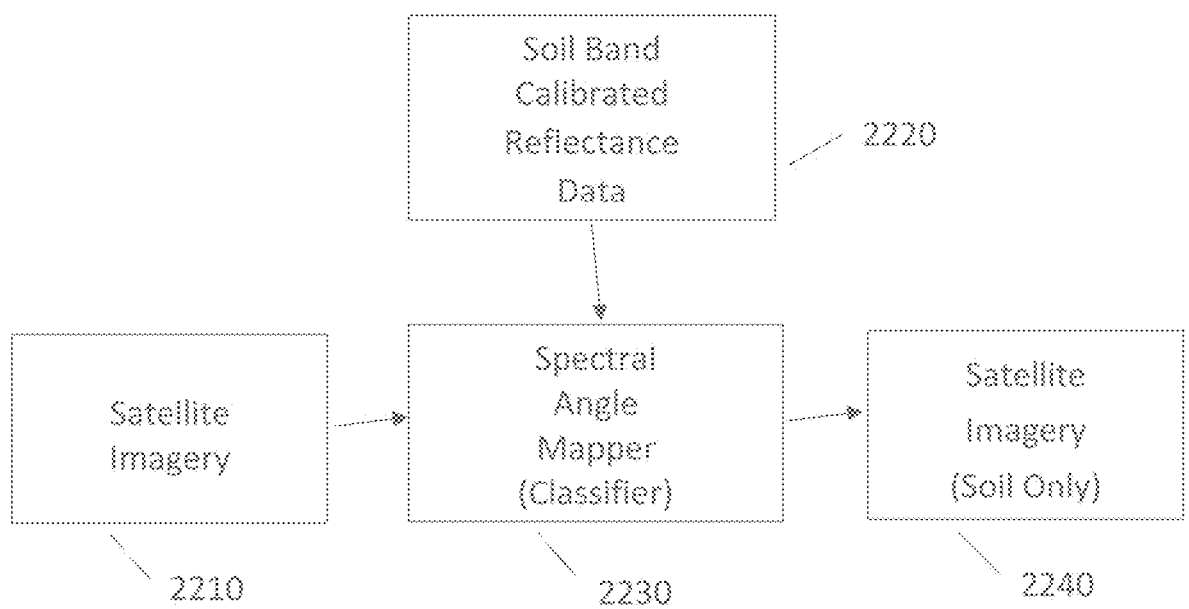
FIG. 21 is a block diagram illustrating a process to identify, from satellite images, soil images separate from tree vegetation images.

FIG. 21 is a block diagram illustrating a process to identify, from satellite images, soil images separate from tree vegetation images. As discussed herein, soil band reflectance data is collected, such as acquired through a field test using spectrometry, as a reference to differentiate tree vegetation from soil in satellite imagery. Satellite imagery 2210 and soil band reflectance data 2220 are input to a processing platform, labeled spectral angle mapper 2230 in FIG. 21. In general, the spectral angle mapper 2230 analyzes the satellite images and uses the soil band reflectance data to classify the pixels of the satellite imagery as either "soil" or "tree vegetation." Block 2240 on FIG. 21 represents the output of the classifier (i.e., only the soil portion of the orchard from the satellite imagery). Although the process is described using a spectral angle mapping technique, any classifier algorithm may be used to differentiate between the soil and tree vegetation without deviating from the spirit and scope of the invention.

Model Integration

Figure 22:
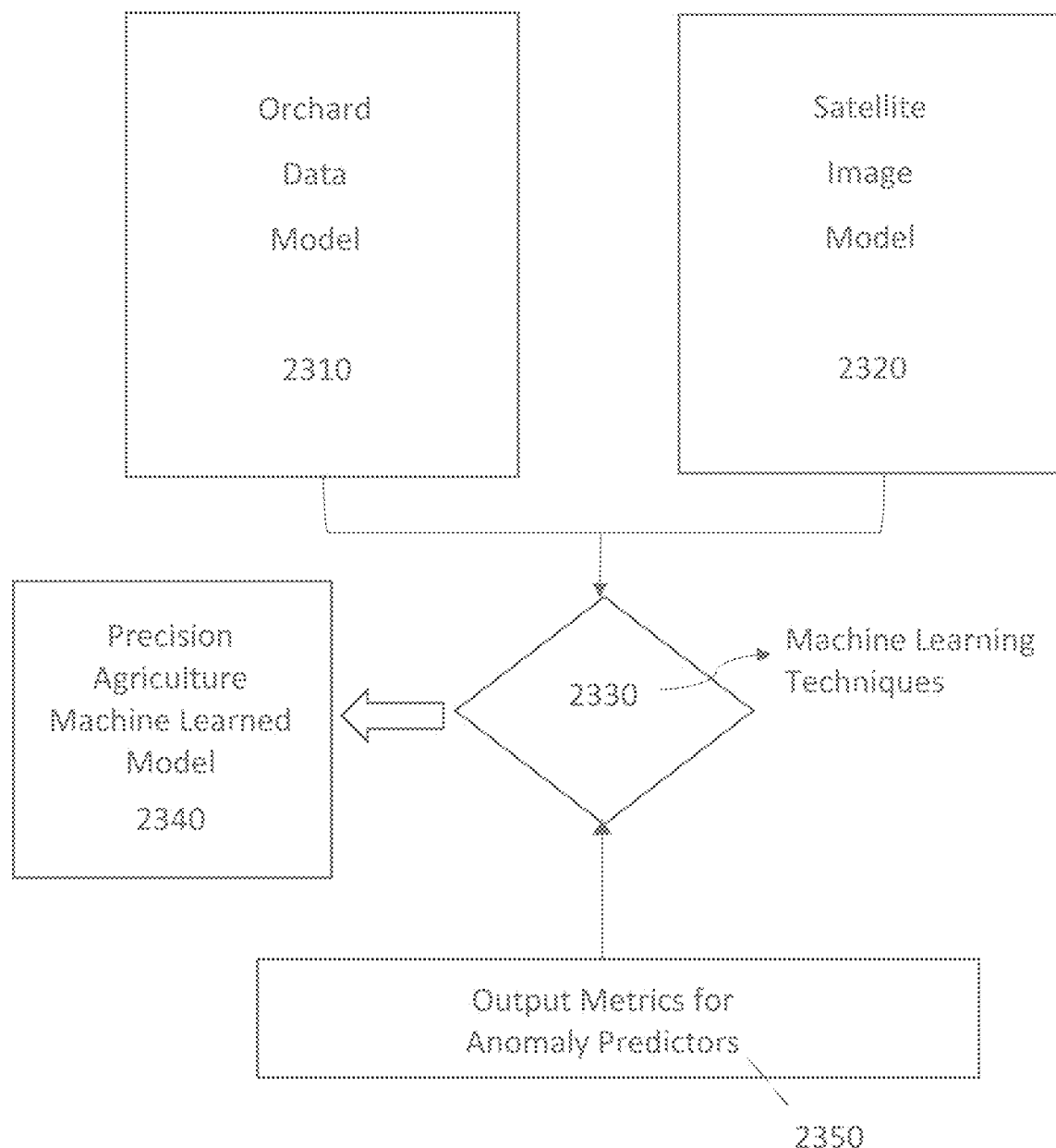
FIG. 22 is a block diagram illustrating one embodiment for integrating an orchard data model and a satellite image model into the precision agriculture machine learned model of the present invention.

FIG. 22 is a block diagram illustrating one embodiment for integrating an orchard data model and a satellite image model into the precision agriculture machine learned model of the present invention. In some embodiments, orchard data model (2310) and satellite image model (2320) may operate as independent predictors for the output conditions. As such, a precision agriculture system that integrates both models provides two prediction mechanisms and, when properly integrated together, enhance the overall predictability of the precision agriculture system. Although the precision agriculture machine learned model is described as combining the orchard data model and the satellite image model, any one, or any combination of both models, may be used to predict one or more output conditions without deviating from the spirit and scope of the invention.

As shown in FIG. 22, orchard data model (2310), satellite image model (2320) and anomaly predictors (2350) (i.e., output conditions) are input to machine-learning techniques processing block (2330). In turn, machine-learning techniques module (2330) executes a learning model to generate precision agriculture machine learned model (2340) by correlating the individual predictions of the orchard data model (2310) and the satellite image model (2320) to the output metrics for the anomaly predictors. Any machine-learning techniques, such as machine learning techniques that use various types of machine-learning algorithms (e.g., nonlinear regression, linear regression, etc.) may be used to establish the relationships among the individual predictions of the orchard data model (2310) and the satellite image model (2320) to the output metrics for the anomaly predictors without deviating from the spirit and scope of the invention. In general, the output metrics may include any type of ground truth data used to validate or calibrate the model(s). For example, output metrics may comprise observed characteristics at an orchard that are known to the farm managers to correlate to specific output conditions. The output metrics may also comprise ground truth data, generated by examining the orchards for which output conditions are predicted and determining the accuracy of the prediction. Embodiments for entering observed characteristics as output metrics into a computer platform for integration into the precision agriculture model are described more fully below. In some embodiments, the orchard data model (2310) and the satellite image model (2320) are integrated and calibrated on an orchard-by-orchard basis (i.e., a unique precision agriculture machine learned model for each orchard). As such, the techniques illustrated in FIG. 22 calibrate the orchard data model and satellite image model for use in predicting output conditions in a specific orchard.

Figure 23:
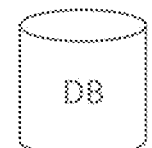
FIG. 23 is a block diagram illustrating a precision agriculture system that incorporates a means to input and integrate farming knowledge.

FIG. 23 is a block diagram illustrating a precision agriculture system that incorporates a means to input and integrate farming knowledge (e.g., output metrics). In some embodiments, the precision agriculture system includes a farming knowledge module (3010) that receives information to integrate agricultural knowledge of one or more orchards, including experience that certain observation of characteristics lead to specific output conditions. Through farming knowledge module (3010), specific farming know-how, developed over a period of time in farming orchards, may be captured, saved and subsequently used in the precision agriculture system. In general, the farming knowledge module (3010), through the user interface (3020), allows a user to input data to characterize know-how related to farming practices for the orchards. In some embodiments, one way for the user to enter farming know-how and observed characteristics as the output metrics is to enter one or more of those characteristics of the orchards, as well as to enter one or more output conditions generally known to follow from the observed characteristics. For example, a farmer may analyze leaf pigmentation in trees, such as red leaf pigmentation, and may have the know-how to identify stress from the leaf pigmentation as a consequence of disease. For this example, the user may input, through the user interface screen (3030), a list of observed conditions for the tress, such as leaf color observations, observations about soil conditions, water, climate, other phenotypic data about the crop. Examples of observed characteristics (e.g., red pigmentation, chlorophyll, leaf senescence, nitrogen levels of soil, observed water conditions, etc.) are shown in the left column in FIG. 23. In addition, the user may enter an output condition associated with the observed conditions, such as disease, as shown on the right hand column of FIG. 23. Similarly, the user, through use of the user interface (3020), may input any observed characteristics potentially affecting the orchards (e.g., tree age, tree density, soil type, soil drainage, phenology phase, yield factor, chill hours, crop quality data, etc.) and a corresponding observed output condition (e.g., disease, soil problem, generic anomalies, salt damage, and healthy bands, water problems, etc.), without deviating from the spirit of scope of the invention.

As shown in FIG. 23, the captured observed characteristics and output conditions are processed in the farming knowledge module (3010) and subsequently stored in a database, such as a relational database, on a physical storage medium (3040). This process, which includes capturing observed characteristics and corresponding output conditions, serves as a means for the precision agriculture system to capture farming expertise, including valuable farming experience and knowledge about orchards, into a database. As described herein, the farming expertise stored in the farming knowledge data store (3040) is used, as ground truth data, to qualify, interpret and train the precision agriculture learned model(s), including used as output metrics to train the orchard data model and the satellite data model.

Figure 24:
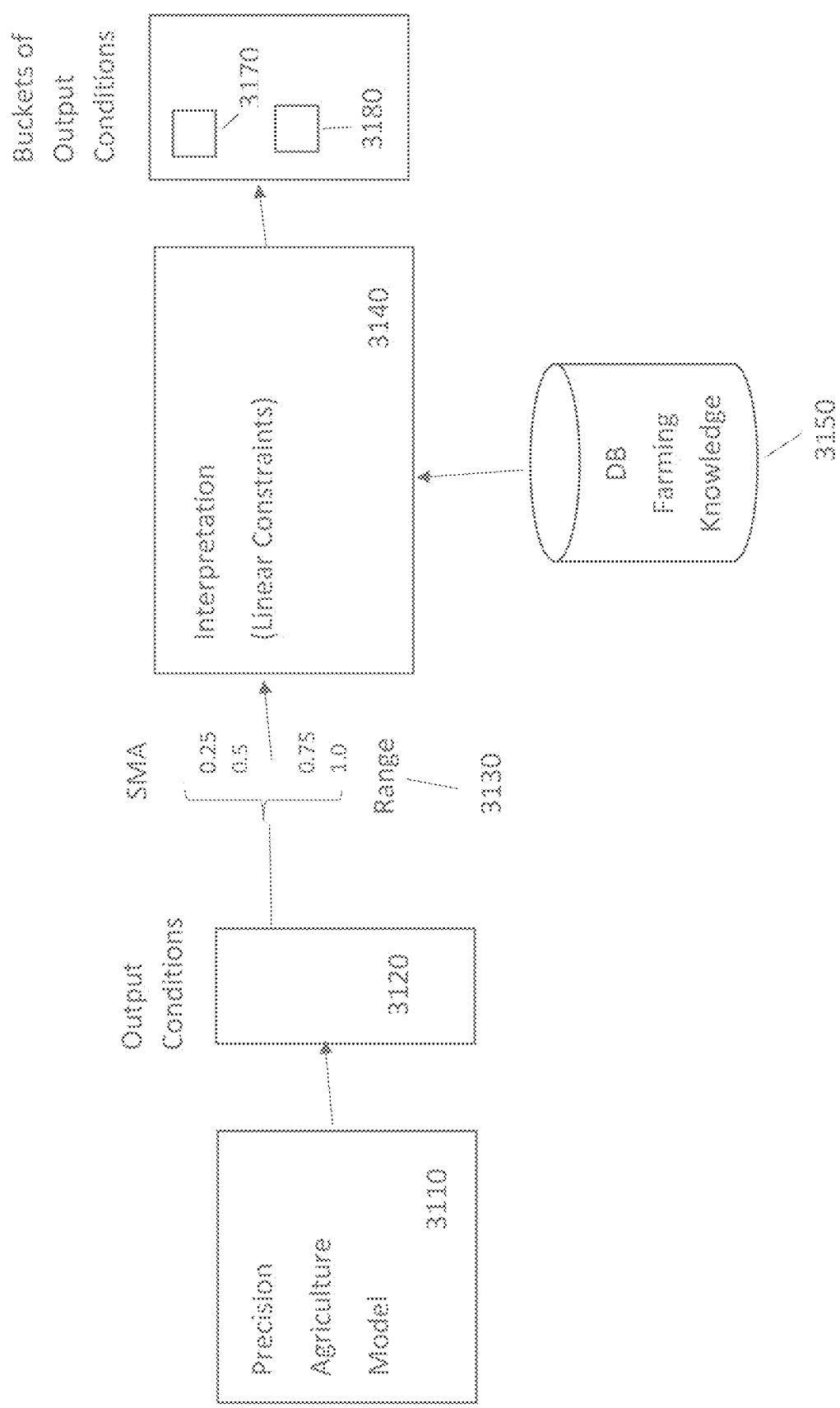
FIG. 24 is a block diagram illustrating one embodiment for using farming knowledge to interpret the output of the precision agriculture learned model.

FIG. 24 is a block diagram illustrating one embodiment for using farming knowledge to interpret the output of the precision agriculture learned model. For this environment, the precision agriculture learned model (3110) predicts various output conditions, such as' disease, soil problem, generic anomalies, salt damage, and healthy bands, water problems, etc.), labeled output conditions 3120. For some embodiments, the output conditions are represented as a range of values, expressed as SMA, that indicate the intensity or strength of the output condition prediction as it correlates to the orchards under analysis. The range of outputs for an output condition is illustrated as a range of SMA values (3130) in FIG. 24. The farming, knowledge database (3150) stores information that correlates one or more observed characteristics of the orchards to one or more output conditions, as described above. In some embodiments, these correlations are used as linear constraints when interpreting a predicted output conditions from the precision agriculture learned model. As shown in FIG. 24, a range of SMA values for a predicted output condition is input to interpretation module (3140). In general, the interpretation module (3140) applies constraints to the predicted output conditions so as to interpret the condition. From this process, the interpretation module (3140) generates buckets of categories (3160) for a predicted output condition, illustrated as buckets (3170) and (3180). For example, one bucket may signify, for a top range of SMA values, an extremely high probability that the output condition exists in the orchards under analysis, while a second bucket may signify, for a second range of SMA values, a lower probability (e.g., 50%) that the output condition exists in the orchards under analysis. In this way, the farming knowledge is integrated into the precision agriculture system to increase the specificity of the output in the ability of the precision agriculture model to predict the output condition in the orchards under analysis.

Precision Agriculture Model

Figure 25:
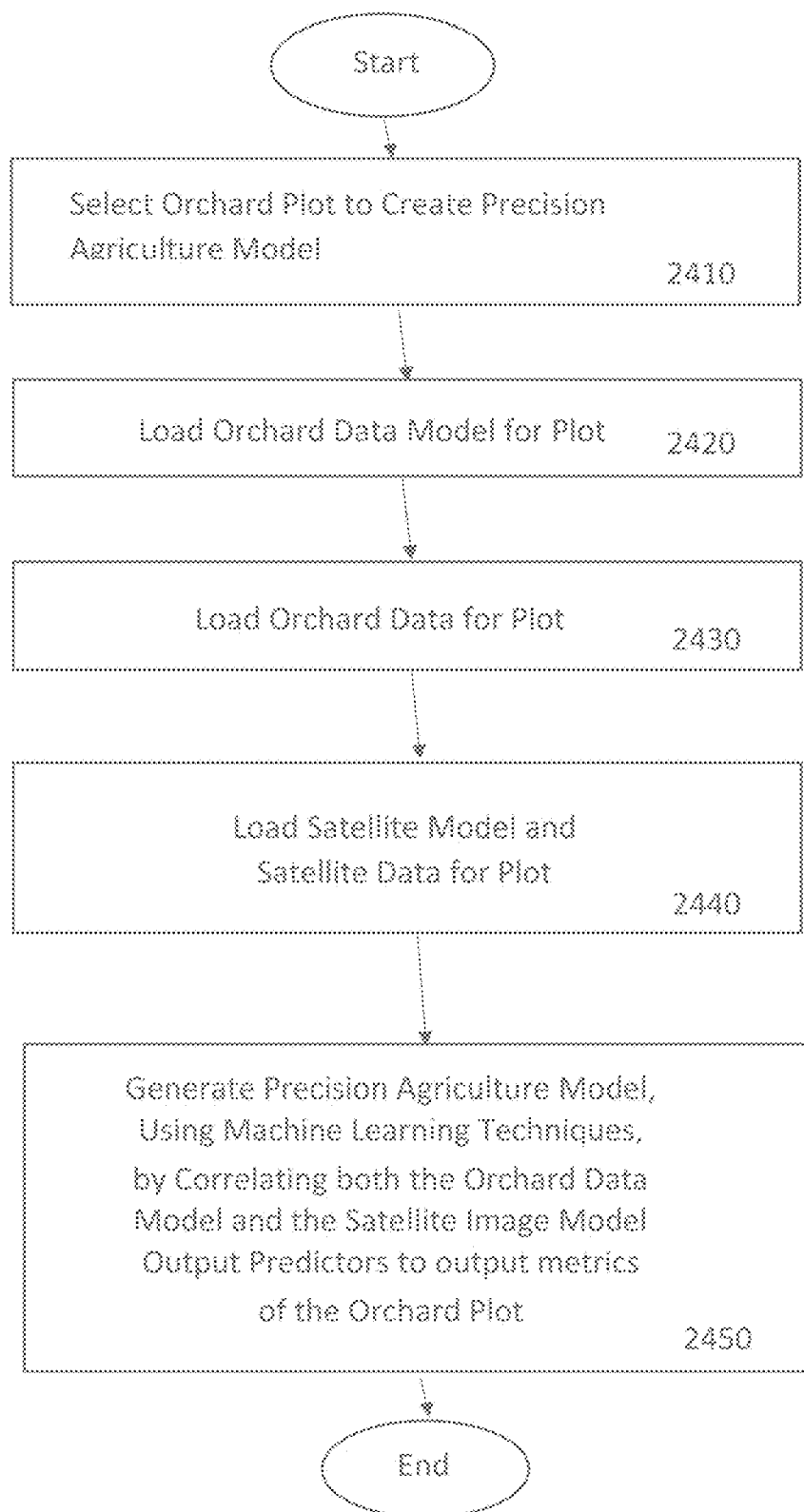
FIG. 25 is a flow diagram illustrating one embodiment for integrating and calibrating a precision agriculture machine learned model.

FIG. 25 is a flow diagram illustrating one embodiment for integrating and calibrating a precision agriculture machine learned model. As discussed above, in some embodiments, a precision agriculture machine learned model is generated for each orchard plot to reflect the unique characteristics of each orchard. To initiate the process, the orchard plot is selected to create the precision agriculture model. A computer platform is used to create the precision agriculture model. The orchard data model and the orchard data for the plot are loaded into the computer platform (blocks 2420 and 2430). Also, the satellite model and satellite imagery are loaded for the orchard plot (block 2440). Machine-learning techniques, running on the computer platform, generate a precision agricultural machine learned model by correlating both the orchard data model and the satellite image model output predictors to the output metrics for the orchard plot (block 2450).

Figure 26:
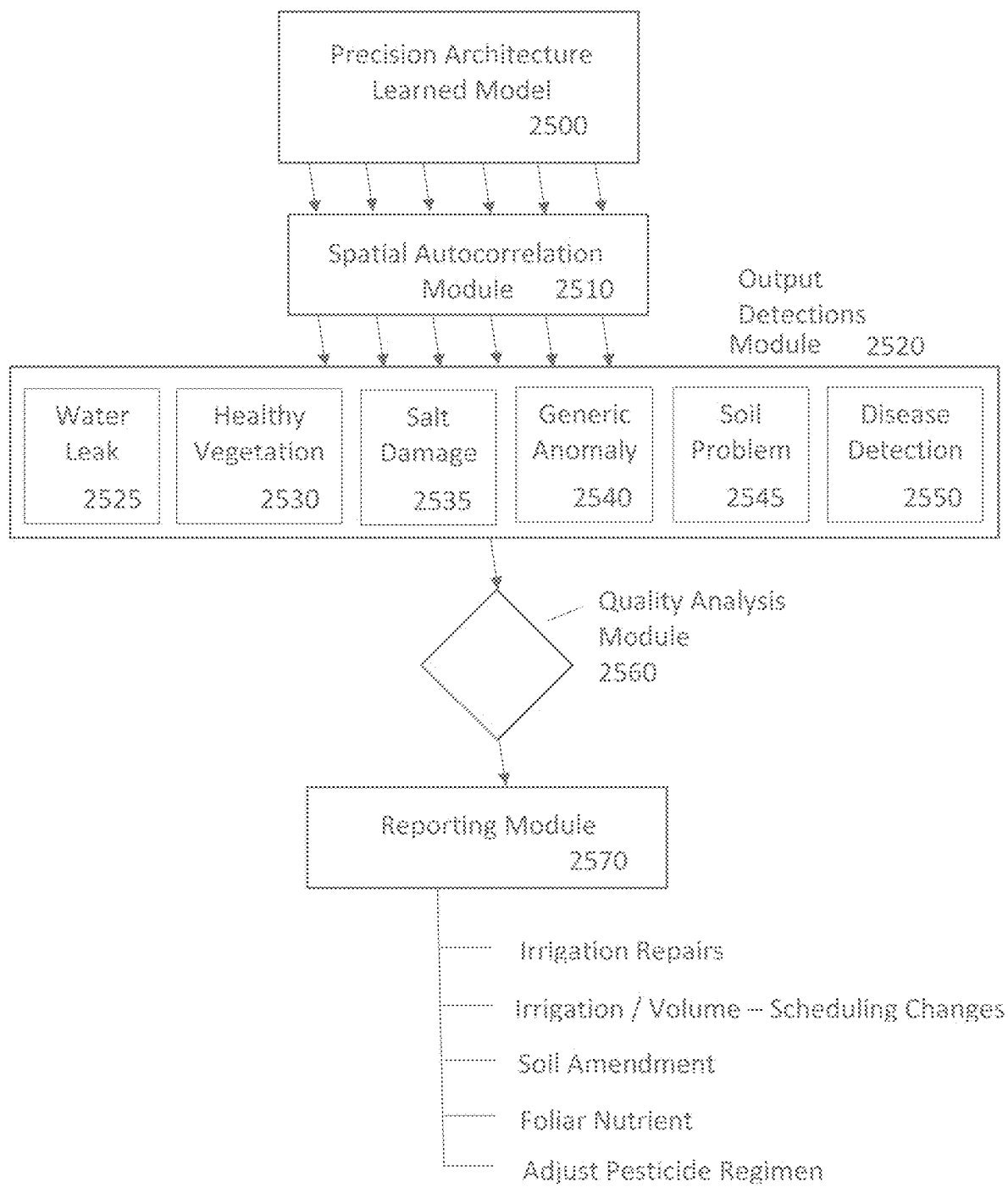
FIG. 26 is a block diagram illustrating one embodiment for a precision agriculture system.

FIG. 26 is a block diagram illustrating one embodiment for a precision agriculture system. As shown in FIG. 26, outputs from precision agriculture machine learned model (2500) are input to spatial autocorrelation processing (2510). In general, the spatial autocorrelation module (2510) processes the output predictions (e.g., output conditions measured) to interpolate the data so as to develop intensity values across the areas of the orchard plot. The interpolation of the data from the precision agriculture learned model allows the data to be mapped across an orchard plot to see "hotspots" for the output prediction. For example, using spatial autocorrelation, the data is mapped to an orchard plot, and severity across the area of the map may be visualized. These hotspots identify areas in the orchard with the output condition.

In some embodiments, the spatial autocorrelation module (2510) uses linear interpolation for generating autocorrelation statistics, such as a spatial statistics model (e.g., Getis-Ord). Although the precision agriculture system discloses use of linear interpolation, any interpolation that generates intensity and severity for orchard plots may be used without deviating from the spirit or scope of the invention. As shown in FIG. 26, the output conditions with the spatial and density are input to the output detection module (e.g., water leak 2525, healthy vegetation 2530, salt damage 2535, generic anomalies 2540, soil problems 2545 and disease detection 2550).

Figure 27:
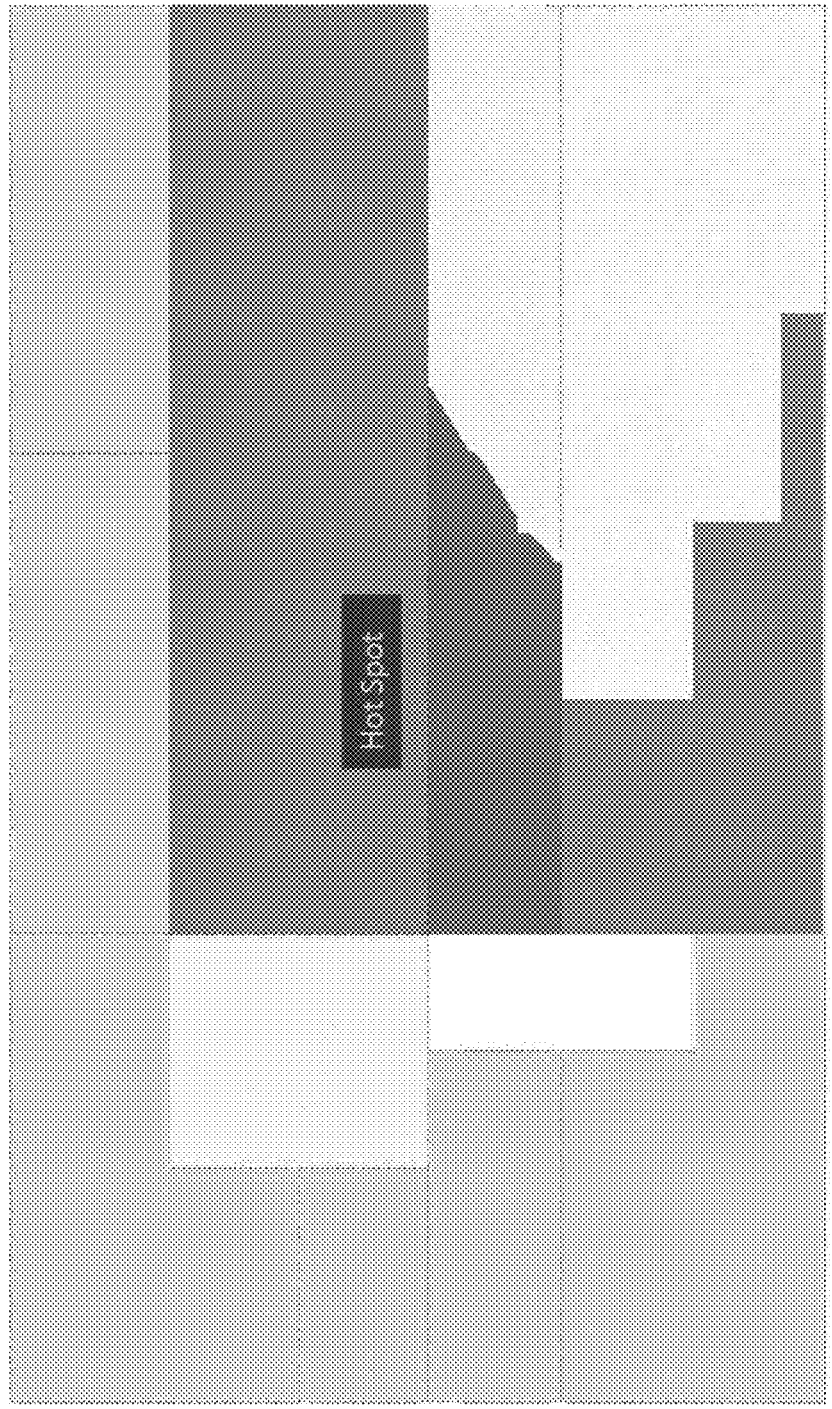
FIG. 27 depicts an output from the hotspot detection module identifying intensity of generic anomalies across an example orchard.

FIG. 27 depicts an output from the hotspot detection module identifying intensity of generic anomalies across an example orchard. The map is coded in gray scale, ranging from dark regions, which identify the intensity of the generic anomalies, to the lighter regions that signify a lower intensity value for generic anomalies.

Figure 28:
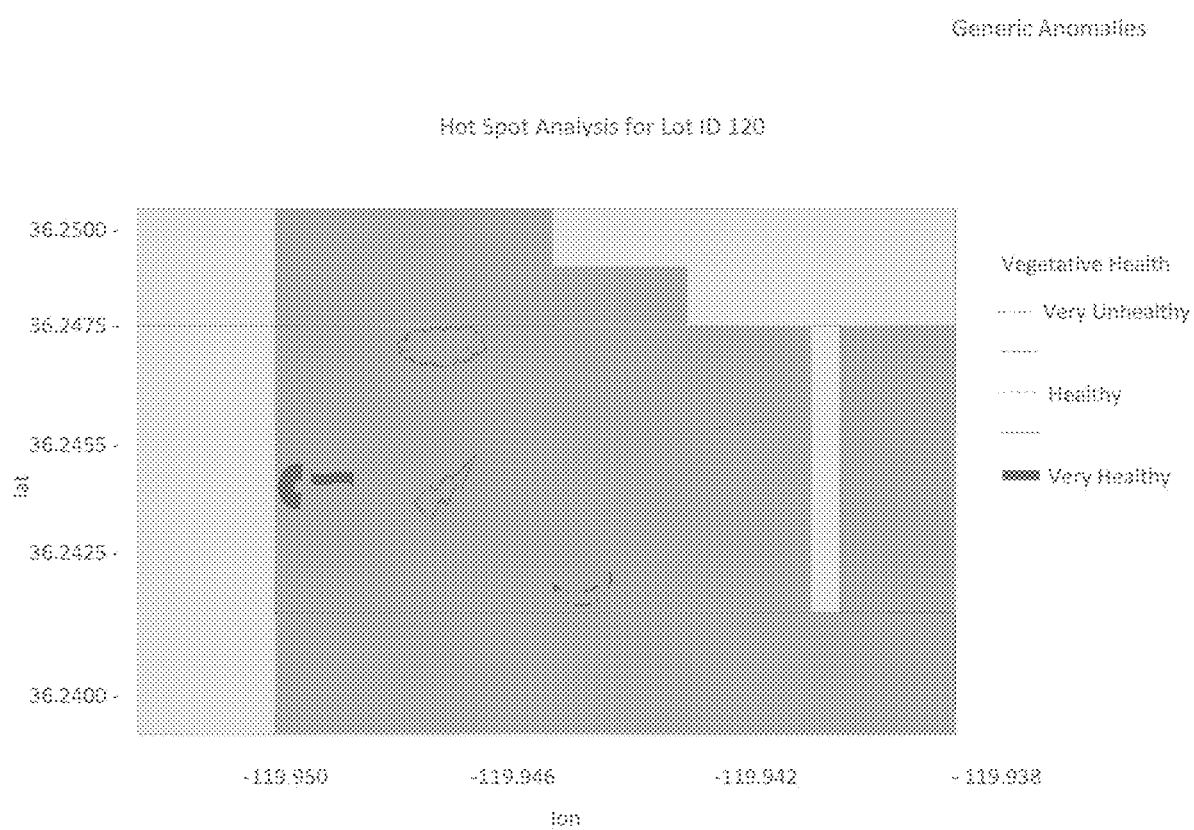
FIG. 28 depicts hotspot analysis based on an analysis of vegetative health.

FIG. 28 depicts hotspot analysis based on an analysis of vegetative health. This output plots a range of vegetative health from very unhealthy to very healthy. The index for the vegetative health is shown next to the corresponding plot for an example orchard.

In general, the precision agriculture model runs data for orchards under analysis to detect one or more output conditions. In some embodiments, the data, associated with the predicted output conditions, may be viewed at different resolutions across one ore more orchard lots under analysis. For example, a graph for an output condition, such as a graph showing generic anomalies, may be plotted to illustrate various intensity levels or hot spots of generic anomalies across several orchard lots, a single orchard, a cluster of trees within an orchard, and even a single tree within an orchard. As such, the precision agriculture system permits a user to extract data ranging from an entire orchard down to a single tree.

Figure 29:
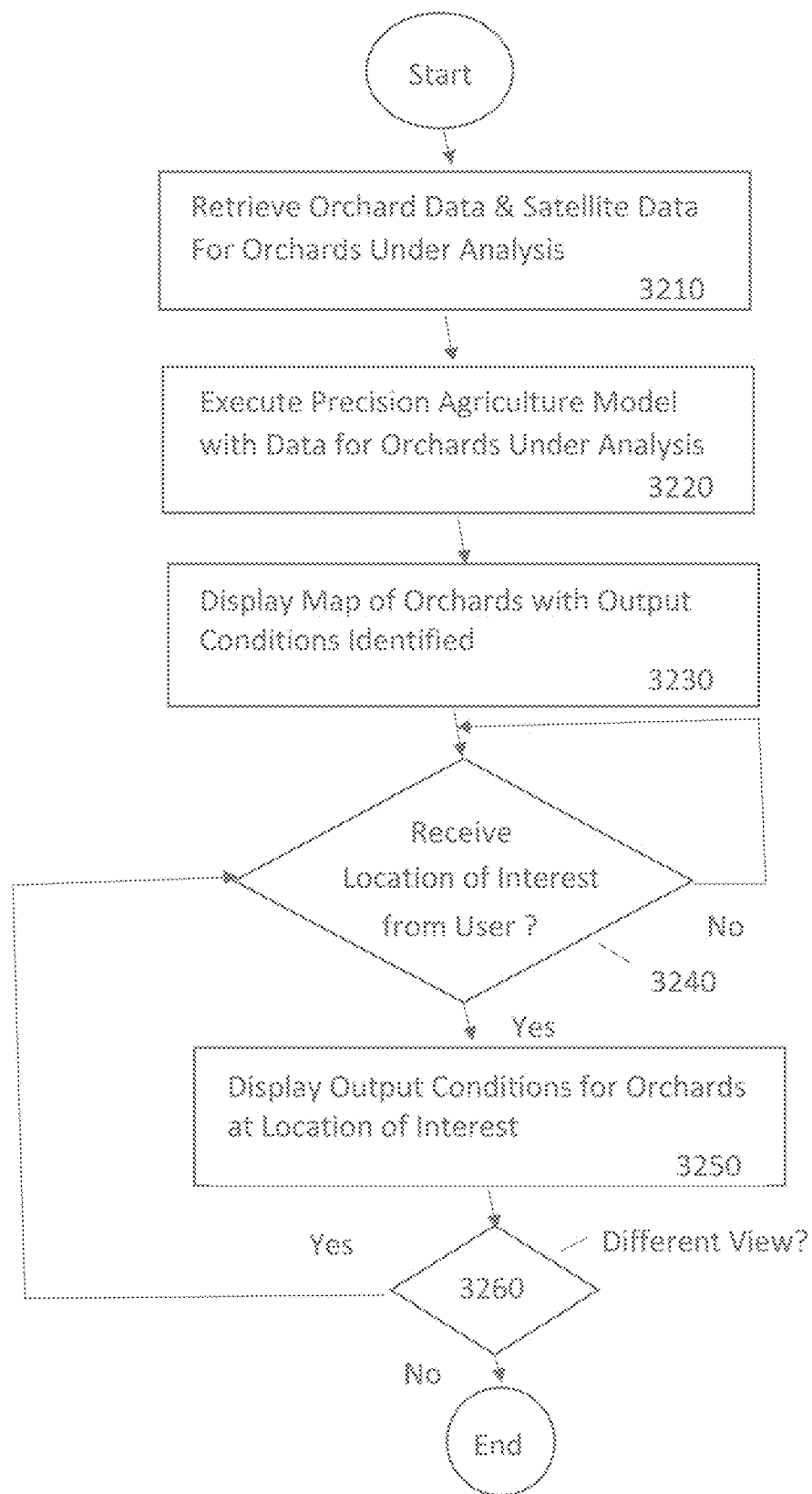
FIG. 29 is a flow diagram illustrating one embodiment for a run time operation executed by the precision agriculture system.

FIG. 29 is a flow diagram illustrating one embodiment for a run time operation executed by the precision agriculture system. Orchard and satellite data are retrieved for orchards under analysis (block 3210). Using the orchard and satellite data, as well as the precision agriculture learned model for the orchards, the precision agriculture model is executed to predict whether one ore more output conditions, associated with the orchards under analysis, exist. In one or more embodiments, the user may view data, on one or more output conditions, at various levels of detail or various resolutions of the orchards under analysis. This feature is illustrated in FIG. 29 in decision block (3240) such that the system receives input from a user to view data associated with output conditions.

The user interface for the module may include any type of interface for the precision agriculture system that receives user input to select resolution of information regarding the output conditions. For example, the precision agriculture system may display a means for a user to select a level of resolution of output conditions on a map. In this way, the user may select specific portions of the orchard to visualize or otherwise extract output condition data. For the embodiment illustrated in FIG. 29, the module displays predicted output conditions for an orchard at the location and resolution specified through the interface (block 3250). For example, if the user desires to extract data down to a specific tree, then the user navigates to the display of the orchard under analysis to select a specific tree to extract any output conditions that exist. Similarly, the user may evaluate sections of an orchard, groups of specific trees, rows or columns of trees, etc. The module, shown in FIG. 29, is an iterative process as the system receives additional input from the user, and in turn, displays output condition for portions of the orchard specified in the request (blocks 3260, 3240 and 3250).

Computer Platform

FIG. 30 depicts a diagrammatic representation of a machine in the exemplary form of a computer system 29A00 within which a set of instructions for causing the machine to perform any one of the methodologies discussed above may be executed. In alternative embodiments, the machine may comprise a network router, a network switch, a network bridge, a personal digital assistant (PDA), a cellular telephone, a web appliance, or any machine capable of executing a sequence of instructions that specify actions to be taken by that machine.

The computer system 29A00 includes a CPU partition having one or more processors (e.g., processor $2902_1$, processor $2902_2$, etc.), a main memory comprising one or more main memory segments (e.g., main memory segment $2904_1$, main memory segment $2904_2$, etc.), and one or more static memories (e.g., static memory $2906_1$, static memory $2906_2$, etc.), any of which components communicate with each other via a bus 2908. The computer system 29A00 may further include one or more video display units (e.g., display unit $2910_1$, display unit $2910_2$, etc.) such as an LED display, or a liquid crystal display (LCD), a cathode ray tube (CRT), etc. The computer system 29A00 can also include one or more input devices (e.g., input device $2912_1$, input device $2912_2$, alphanumeric input device, keyboard, pointing device, mouse, etc.), one or more database interfaces (e.g., database interface $2914_1$, database interface $2914_2$, etc.), one or more disk drive units (e.g., drive unit $2916_1$, drive unit $2916_2$, etc.), one or more signal generation devices (e.g., signal generation device $2918_1$, signal generation device $2918_2$, etc.), and one or more network interface devices (e.g., network interface device $2920_1$, network interface device $2920_2$, etc.).

The disk drive units can include one or more instances of a machine-readable medium 2924 on which is stored one or more instances of a data table 2919 to store electronic information records. The machine-readable medium 2924 can further store a set of instructions $2926_0$ (e.g., software) embodying any one, or all, of the methodologies described above.

A set of instructions $2926_1$ can also be stored within the main memory (e.g., in main memory segment $2904_1$). Further, a set of instructions $2926_2$ can also be stored within the one or more processors (e.g., processor $2902_1$). Such instructions and/or electronic information may further be transmitted or received via the network interface devices at one or more network interface ports (e.g., network interface port $2923_1$, network interface port $2923_2$, etc.). Specifically, the network interface devices can communicate electronic information across a network using one or more optical links, Ethernet links, wireline links, wireless links, and/or other electronic communication links (e.g., communication link $2922_1$, communication link $2922_2$, etc.). One or more network protocol packets (e.g., network protocol packet $2921_1$, network protocol packet $2921_2$, etc.) can be used to hold the electronic information (e.g., electronic data records) for transmission across an electronic communications network (e.g., network 2948). In some embodiments, the network 2948 may include, without limitation, the web (i.e., the Internet), one or more local area networks (LANs), one or more wide area networks (WANs), one or more wireless networks, and/or one or more cellular networks.

The computer system 29A00 can be used to implement a client system and/or a server system, and/or any portion of network infrastructure.

It is to be understood that various embodiments may be used as, or to support, software programs executed upon some form of processing core (such as the CPU of a computer) or otherwise implemented or realized upon or within a machine or computer readable medium. A machine-readable medium includes any mechanism for storing or transmitting information in a form readable by a machine (e.g., a computer). For example, a machine-readable medium includes read-only memory (ROM), random access memory (RAM), magnetic disk storage media, optical storage media, flash memory devices, or any other type of non-transitory media suitable for storing or transmitting information.

A module as used herein can be implemented using any mix of any portions of the system memory, and any extent of hard-wired circuitry including hard-wired circuitry embodied as one or more processors (e.g., processor $2902_1$, processor $2902_2$, etc.).

What is claimed is:

1. A computer-implemented method for predicting at least one output condition for precision agriculture management of permanent crops, comprising:
    storing, in a computer platform, a plurality of site and crop datasets for a plurality of lots with permanent crops, wherein the site and crop datasets comprise a plurality of variables with data values from at least one of the following types of site and crop datasets: tree age, alternative bearing factor and phenology;
    storing, in a computer platform, at least one output metric dataset comprising at least one output metric that characterizes an output condition comprising at least one of the following output conditions: detecting disease, detecting salt damage, detecting soil problems, and detecting generic anomalies;
    executing, on the computer platform, machine-learning techniques, to generate an orchard data learned model to predict at least one of the output conditions by discovering a plurality of buckets that delineate a plurality of ranges of the data values associated with the variables of the site and crop dataset, and by correlating the buckets of the data values for the variables to one or more of the output metrics;
    loading, in a computer platform, at least one site and crop dataset associated with one or more lots under analysis; and
    executing, in the computer platform, the orchard data learned model with the site and crop datasets associated with the lot under analysis by assigning the data values from the variables of the site and crop dataset for the lot under analysis to the buckets in the orchard data learned model and by predicting whether at least one of the output conditions exist for the lot under analysis.

2. The computer-implemented method as set forth in claim 1, wherein executing, on the computer platform, machine-learning techniques to discover a plurality of buckets comprises executing, on the computer platform, machine-learning techniques to discover, for the tree age dataset, a 6-10 year bucket, an 11-25 year bucket and a greater than 25 year bucket.

3. The computer-implemented method as set forth in claim 1, wherein the site and crop datasets further comprise site and crop datasets for tree density, soil, weather, quality and yield.

4. The computer-implemented method as set forth in claim 3, wherein executing, on the computer platform, machine-learning techniques to discover a plurality of buckets comprises executing, on the computer platform, machine-learning techniques to discover, for the tree density dataset, a less than 125 trees per acre bucket, a 126-145 trees per acre bucket, and greater than 145 trees per acre bucket.

5. The computer-implemented method as set forth in claim 3, wherein executing, on the computer platform, machine-learning techniques to discover a plurality of buckets comprises executing, on the computer platform, machine-learning techniques to discover, for the soil dataset, a sandy type bucket, a loam type bucket and a clay type bucket.

6. The computer-implemented method as set forth in claim 3, wherein executing, on the computer platform, machine-learning techniques to discover a plurality of buckets comprises executing, on the computer platform, machine-learning techniques to discover, for the soil dataset, a well drained type bucket, an average drained type bucket and poorly drained type bucket.

7. The computer-implemented method as set forth in claim 3, wherein:
    storing the weather type of site and crop datasets comprises storing chilling hours for the orchard lots; and
    executing, on the computer platform, machine-learning techniques to discover a plurality of buckets comprises executing, on the computer platform, machine-learning techniques to discover, for the chilling hours dataset, a less than 800 hours bucket, a 801 to 1000 hours bucket, and a greater than 1000 hours bucket.

8. The computer-implemented method as set forth in claim 3, wherein executing, on the computer platform, machine-learning techniques to discover a plurality of buckets comprises executing, on the computer platform, machine-learning techniques to discover, for the quality dataset, insect, trash, blanks, stain and adhering quality bins and high and low buckets.

9. The computer-implemented method as set forth in claim 1, wherein executing, on the computer platform, machine-learning techniques to discover a plurality of buckets comprises executing, on the computer platform, machine-learning techniques to discover, for the phenology dataset, a low phenology phase bucket, a rapid rise phenology phase bucket, a flat phenology phase bucket and a declining phenology phase bucket.

10. A computer readable medium, embodied in a non-transitory computer readable medium, the non-transitory computer readable medium having stored thereon a sequence of instructions which, when stored in memory and executed by a processor causes the processor to perform a set of acts, the acts comprising:
    storing, in a computer platform, a plurality of site and crop datasets for a plurality of lots with permanent crops, wherein the site and crop datasets comprise a plurality of variables with data values from at least one of the following types of site and crop datasets: tree age, alternative bearing factor and phenology;

storing, in a computer platform, at least one output metric dataset comprising at least one output metric that characterizes an output condition comprising at least one of the following output conditions: detecting disease, detecting salt damage, detecting soil problems, and detecting generic anomalies;

executing, on the computer platform, machine-learning techniques, to generate an orchard data learned model to predict at least one of the output conditions by discovering a plurality of buckets that delineate a plurality of ranges of the data values associated with the variables of the site and crop dataset, and by correlating the buckets of the data values for the variables to one or more of the output metrics;

loading, in a computer platform, at least one site and crop dataset associated with one or more lots under analysis; and executing, in the computer platform, the orchard data learned model with the site and crop datasets associated with the lot under analysis by assigning the data values from the variables of the site and crop dataset for the lot under analysis to the buckets in the orchard data learned model and by predicting whether at least one of the output conditions exist for the lot under analysis.

11. The computer readable medium as set forth in claim 10, wherein executing, on the computer platform, machine-learning techniques to discover a plurality of buckets comprises executing, on the computer platform, machine-learning techniques to discover, for the tree age dataset, a 6-10 year bucket, an 11-25 year bucket and a greater than 25 year bucket.

12. The computer readable medium as set forth in claim 10, wherein the site and crop datasets further comprise site and crop datasets for tree density, soil, weather, quality and yield.

13. The computer readable medium as set forth in claim 12, wherein executing, on the computer platform, machine-learning techniques to discover a plurality of buckets comprises executing, on the computer platform, machine-learning techniques to discover, for the tree density dataset, a less than 125 trees per acre bucket, a 126-145 trees per acre bucket, and greater than 145 trees per acre bucket.

14. The computer readable medium as set forth in claim 12, wherein executing, on the computer platform, machine-learning techniques to discover a plurality of buckets comprises executing, on the computer platform, machine-learning techniques to discover, for the soil dataset, a sandy type bucket, a loam type bucket and a clay type bucket.

15. The computer readable medium as set forth in claim 12, wherein executing, on the computer platform, machine-learning techniques to discover a plurality of buckets comprises executing, on the computer platform, machine-learning techniques to discover, for the soil dataset, a well drained type bucket, an average drained type bucket and poorly drained type bucket.

16. The computer readable medium as set forth in claim 12, wherein:
storing the weather type of site and crop datasets comprises storing chilling hours for the orchard lots; and
executing, on the computer platform, machine-learning techniques to discover a plurality of buckets comprises executing, on the computer platform, machine-learning techniques to discover, for the chilling hours dataset, a less than 800 hours bucket, a 801 to 1000 hours bucket, and a greater than 1000 hours bucket.

17. The computer readable medium as set forth in claim 10, wherein executing, on the computer platform, machine-learning techniques to discover a plurality of buckets comprises executing, on the computer platform, machine-learning techniques to discover, for the phenology dataset, a low phenology phase bucket, a rapid rise phenology phase bucket, a flat phenology phase bucket and a declining phenology phase bucket.

18. A system comprising:
a storage medium, having stored thereon, a sequence of instructions;
at least one processor, coupled to the storage medium, that executes the instructions to causes the processor to perform a set of acts comprising:
storing, in a computer platform, a plurality of site and crop datasets for a plurality of lots with permanent crops, wherein the site and crop datasets comprise a plurality of variables with data values from at least one of the following types of site and crop datasets: tree age, alternative bearing factor and phenology;
storing, in a computer platform, at least one output metric dataset comprising at least one output metric that characterizes an output condition comprising at least one of the following output conditions: detecting disease, detecting salt damage, detecting soil problems, and detecting generic anomalies;
executing, on the computer platform, machine-learning techniques, to generate an orchard data learned model to predict at least one of the output conditions by discovering a plurality of buckets that delineate a plurality of ranges of the data values associated with the variables of the site and crop dataset, and by correlating the buckets of the data values for the variables to one or more of the output metrics;
loading, in a computer platform, at least one site and crop dataset associated with one or more lots under analysis; and
executing, in the computer platform, the orchard data learned model with the site and crop datasets associated with the lot under analysis by assigning the data values from the variables of the site and crop dataset for the lot under analysis to the buckets in the orchard data learned model and by predicting whether at least one of the output conditions exist for the lot under analysis.

* * * * *